US010945799B2

(12) United States Patent
Wada

(10) Patent No.: US 10,945,799 B2
(45) Date of Patent: Mar. 16, 2021

(54) MANIPULATOR SYSTEM

(71) Applicant: Olympus Corporation, Hachioji (JP)

(72) Inventor: Toru Wada, Saitama (JP)

(73) Assignee: OLYMPUS CORPORATION, Tokyo (JP)

(*) Notice: Subject to any disclaimer, the term of this patent is extended or adjusted under 35 U.S.C. 154(b) by 225 days.

(21) Appl. No.: 16/189,464

(22) Filed: Nov. 13, 2018

(65) Prior Publication Data
US 2019/0083189 A1 Mar. 21, 2019

Related U.S. Application Data

(63) Continuation of application No. PCT/JP2016/088951, filed on Dec. 27, 2016.

(51) Int. Cl.
*A61B 34/37* (2016.01)
*A61B 34/00* (2016.01)
(Continued)

(52) U.S. Cl.
CPC .......... *A61B 34/37* (2016.02); *A61B 18/1492* (2013.01); *A61B 34/70* (2016.02); *A61B 34/71* (2016.02); *B25J 9/1674* (2013.01); *A61B 2017/00477* (2013.01); *A61B 2018/00208* (2013.01); *A61B 2018/00672* (2013.01); *A61B 2018/00678* (2013.01);
(Continued)

(58) Field of Classification Search
CPC ...................... A61B 34/37; G05B 2219/45118
See application file for complete search history.

(56) References Cited

U.S. PATENT DOCUMENTS 9,375,288 B2 * 6/2016 Robinson ........... A61B 18/1206
10,149,726 B2 * 12/2018 Hibner .................. A61B 34/71
(Continued)

FOREIGN PATENT DOCUMENTS

JP 2006-055927 3/2006
JP 2010-022415 2/2010
(Continued)

OTHER PUBLICATIONS

Decision to Grant a Patent from corresponding Japanese Application No. 2018-558580 dated Jan. 2, 2020.
(Continued)

*Primary Examiner* — Eduardo Colon Santana
*Assistant Examiner* — Devon A Joseph
(74) *Attorney, Agent, or Firm* — Scully, Scott, Murphy & Presser, P.C.

(57) ABSTRACT

A manipulator system includes arithmetic logic units for calculating an operation quantity per unit time of a power source mounted on a surgical instrument as a first operation quantity and calculating an operation quantity per unit time of the power source as a second operation quantity. A determining unit is used for outputting a shutoff signal for de-energizing the power source if the first operation quantity is smaller than a first threshold value and the second operation quantity is larger than a second threshold value. A cutoff unit is configured to cut off the drive signal output from the output unit to the power source in response to the shutoff signal output for de-energizing the power source from the determining unit.

8 Claims, 17 Drawing Sheets

(51) Int. Cl.
*A61B 18/14* (2006.01)
*B25J 9/16* (2006.01)
*A61B 34/30* (2016.01)
*A61B 90/00* (2016.01)
*A61B 17/00* (2006.01)
*A61B 18/00* (2006.01)

(52) U.S. Cl.
CPC .............. *A61B 2018/00708* (2013.01); *A61B 2018/00827* (2013.01); *A61B 2018/00898* (2013.01); *A61B 2034/301* (2016.02); *A61B 2034/302* (2016.02); *A61B 2090/0808* (2016.02); *G05B 2219/45118* (2013.01)

(56) References Cited

U.S. PATENT DOCUMENTS

| | | | | |
|---|---|---|---|---|
| 10,405,931 | B2* | 9/2019 | Fukushima | A61B 34/30 |
| 2014/0039519 | A1* | 2/2014 | Inoue | A61B 34/30 606/130 |
| 2014/0228862 | A1* | 8/2014 | Inoue | A61B 34/37 606/130 |
| 2016/0213224 | A1* | 7/2016 | Hatakeyama | A61B 34/70 |
| 2018/0099422 | A1* | 4/2018 | Yoon | B25J 13/084 |
| 2019/0083189 | A1* | 3/2019 | Wada | B25J 9/1674 |

FOREIGN PATENT DOCUMENTS

| | | |
|---|---|---|
| JP | 2012-061195 | 3/2012 |
| JP | 2012-235936 | 12/2012 |
| JP | 2013-094452 | 5/2013 |
| JP | 2016-208656 | 12/2016 |
| WO | 2015-012142 | 1/2015 |
| WO | 2016-204099 | 12/2016 |

OTHER PUBLICATIONS

International Search Report and Written Opinion from corresponding International Application No. PCT/JP2016/088951 dated Mar. 21, 2017.

* cited by examiner

MANIPULATOR SYSTEM

CROSS-REFERENCE TO RELATED APPLICATIONS

This application is a continuation application of PCT Application No. PCT/JP 2016/088951 filed on Dec. 27, 2016, which is hereby incorporated by reference in its entirety.

TECHNICAL FIELD

The technology disclosed herein relates to a manipulator system.

DESCRIPTION OF THE RELATED ART

There have been known medical manipulators for treating a tissue in a body of a patient under remote control. Generally, the medical manipulators have a safety device for preventing them from malfunctioning due to a failure of parts that make up the manipulators. For example, Japanese Patent JP 2013-094452A discloses a surgery supporting apparatus having a controller for detecting a failure of one surgical instrument mounted on a manipulator using a plurality of encoders provided on the surgical instrument. The surgery supporting apparatus revealed in JP 2013-0944521 calculates a difference between operation quantities of the surgical instrument that are detected by the encoders. The surgery supporting apparatus compares the difference with a predetermined threshold value to detect a failure of at least one of the encoders. Upon detection of the failure of the encoder, the surgery supporting apparatus disclosed in JP 2013-094452 brings the surgical instrument to a secure stop.

According to the technology disclosed in JP 2013-094452, it is determined that there is a failure in an encoder in the event that the difference between the operation quantities detected by the respective encoders increases in excess of the threshold value. The surgical instrument operates despite the failure immediately after the failure occurred in the encoder until the difference exceeds the threshold value. Therefore, in the event of a failure of the transmission of power to the surgical instrument, it is required to shorten the time from the occurrence of the failure to the shutdown of the surgical instrument. Therefore, there is a need for a manipulator system that can be safely operated in the event of the failure of the transmission of power to the surgical instrument.

BRIEF SUMMARY OF EMBODIMENTS

The technology disclosed herein is directed to a manipulator system capable of making a quick transition to a safe state in the event of a failure of the transmission of power to a surgical instrument thereof.

According to one aspect of the technology disclosed herein, a manipulator system includes a power source, a first sensor, a second sensor, an arithmetic logic unit, an operation input device, a control signal generator, an output unit, a determining unit, and a cutoff unit all of which are directly or indirectly interconnected to one another for treating a tissue in a body of a patient. The power source is configured to generate drive power for operating a surgical instrument. The first sensor is configured to detect a first detected value corresponding to a drive quantity of the power source. The second sensor is configured to detect a second detected value corresponding to the drive quantity of the power source. An arithmetic logic unit is configured to calculate a first operation quantity of the power source per unit time based on the first detected value. The arithmetic logic unit is configured to calculate a second operation quantity of the power source per unit time based on the second detected value. The operation input device is operable by a user for executing an input command. The control signal generator is configured to receive a signal output from the operation input device and generate a control signal for operating the surgical instrument. The output unit is configured to receive the control signal generated by the control signal generator and generate a drive signal for energizing the power source. The determining unit is configured to output a shutoff signal for de-energizing the power source if the first operation quantity is smaller than a first threshold value and the second operation quantity is larger than a second threshold value. The cutoff unit is configured to cut off the drive signal output from the output unit to the power source in response to the shutoff signal output for de-energizing the power source from the determining unit.

The determining unit may output the shutoff signal if the absolute value of the difference between the first operation quantity calculated based on the first detected value and the second operation quantity calculated based on the second detected value is larger than a third threshold value, in the event that the first operation quantity is larger than the first threshold value or the second operation quantity is smaller than the second threshold value. The power source may be detachably attached to the surgical instrument. The power source may be capable of transmitting the drive power to the surgical instrument when the power source is attached to the surgical instrument. The power source may have one or more connect/disconnect sensor configured to output a signal to the determining unit when the surgical instrument and the power source are attached to each other. The determining unit may output the shutoff signal if the signal is input to the determining unit and if the first operation quantity is smaller than the first threshold value and the second operation quantity is larger than the second threshold value. The first threshold value may be equal to or smaller than the second threshold value.

The manipulator system according to the aforementioned aspect may further include an operation unit configured to operate the surgical instrument. The surgical instrument may have an electrode for treating a tissue. The operation unit may have a switch for selectively turning on and off the supply of an electric current to the electrode. The determining unit may output the shutoff signal based on the result of comparison between a third threshold value and the absolute value of the difference between (i) the operation quantity calculated based on the first detected value and (ii) the operation quantity calculated based on the second detected value, in the event that the supply of an electric current to the electrode is turned off. The determining unit may output the shutoff signal if (i) the first operation quantity is smaller than the first threshold value and (ii) the second operation quantity is larger than the second threshold value, in the event that the supply of an electric current to the electrode is turned on.

According to another aspect of the technology disclosed herein, a manipulator system includes an elongated member, an operation input device, a drive unit, a transmitted member, a first sensor, a second sensor, and at least one manipulator control device. The elongated member includes at least one joint. The operation input device is operable by a user for entering an input. The drive unit is configured to output drive power for actuating the joint in response to the input from the operation input device. The drive power is transmitted from the drive unit to the transmitted member. The transmitted member is rotatable by the drive power. The first sensor is configured to be mounted on the drive unit. The first sensor is configured to detect over time an angular displacement of the drive unit when the drive unit actuates the joint. The first sensor is configured to output a first detected value representing the detected angular displacement. The second sensor is configured to be mounted on the transmitted member. The second sensor is configured to detect over time an angular displacement of the transmitted member when the drive unit actuates the joint. The second sensor is configured to output a second detected value representing the detected angular displacement. The at least one manipulator control device is configured to calculate a first difference and a second difference. The first difference represents an amount of change in the angular displacement with respect to time change based on the first detected value. The second difference represents an amount of change in the angular displacement with respect to time change based on the second detected value. The at least one manipulator control device compares the first difference and a first threshold value with one another and compares the second difference and a second threshold value with another. The at least one manipulator control device controls the drive unit to de-energize the drive unit if the first difference is smaller than the first threshold value and the second difference is larger than the second threshold value. Accordingly, the manipulator system disclosed herein is capable of making a quick transition to a safe state in the event of a failure.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

Figure 1:
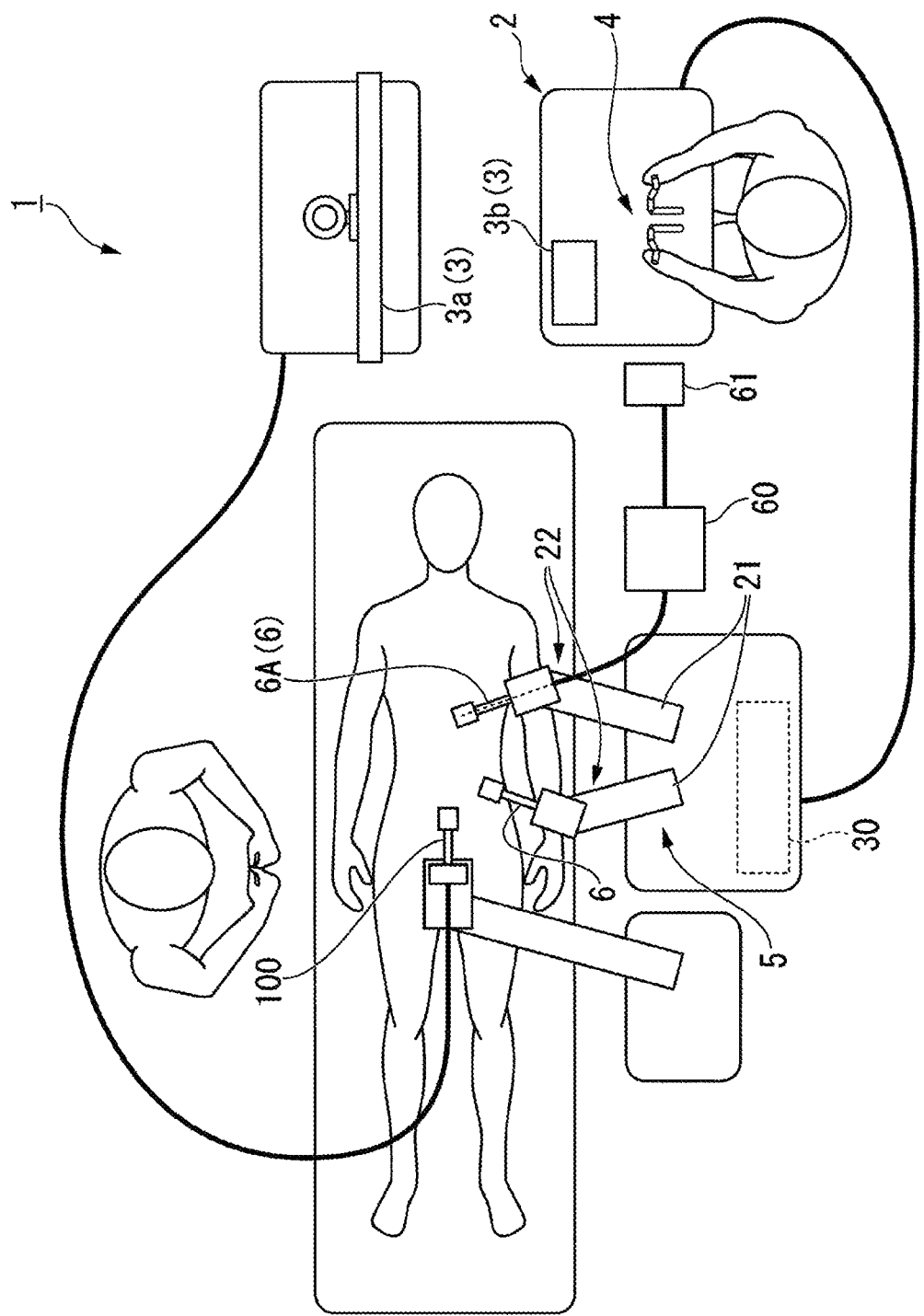
FIG. 1 is a top view of a manipulator system according to a first embodiment of the technology disclosed herein.

A first embodiment is described hereinafter with reference to FIGS. 1 through 11 in which FIG. 1 is a general view of the manipulator system according to the present embodiment.

The manipulator system 1, includes an operation input device 2, a manipulator 5, and a manipulator control device 30 all of which are directly or indirectly connected to one another to operate on a body of a patient. An operation input command is applied by a user to the operation input device 2. The manipulator 5 performs a treatment or the like in the body of the patient according to an operation input command applied to the operation input device 2. The manipulator control device 30 controls the manipulator 5 to operate according to an operation input command applied to the operation input device 2. The operation input device 2 functions as a master for transmitting an operation movement of the user, e.g., a surgeon, to the manipulator 5. The operation input device 2 includes a display unit 3 and an operation unit 4. The display unit 3 includes a monitor 3a and a monitor 3b. The monitor 3a displays a video image of a surgical region of the patient and its neighborhood which is captured by a laparoscope 100. The monitor 3b displays an error message, and the like issued by the manipulator system 1. The operation unit 4 is connected to the manipulator control device 30 for communication therewith so that the operation unit 4 can transmit an operation movement of the user to the manipulator 5. When the operation unit 4 is operated by the user, the operation unit 4 outputs an operation signal to the manipulator control device 30 for actuating the manipulator 5 in accordance with the movement of the user who operates the operation unit 4. The manipulator 5 includes a plurality of surgical instruments 6 and drive units 22 for moving the respective surgical instruments 6. The surgical instruments 6 are controlled for their movements based on control signals output from the manipulator control device 30.

Figure 2:
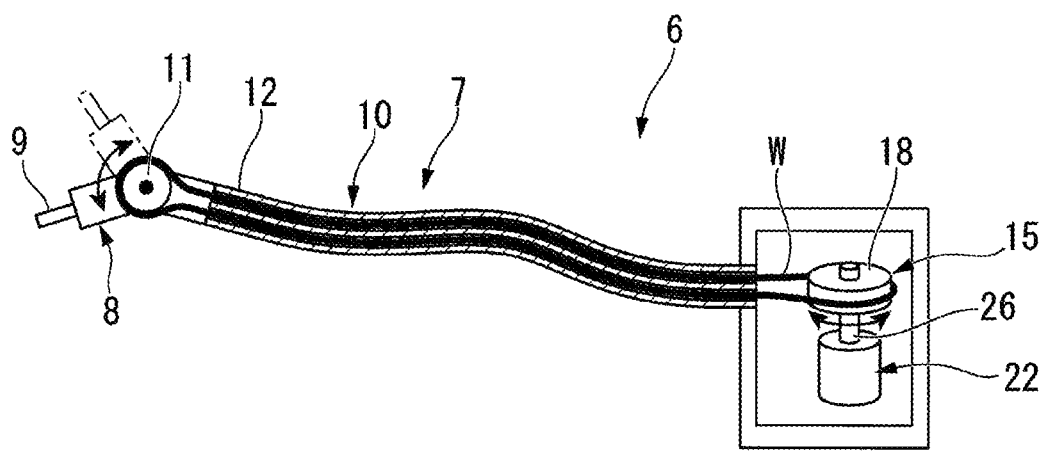
FIG. 2 is a schematic view depicting a surgical instrument of the manipulator system.

FIG. 2 is a schematic view depicting each of the surgical instruments 6 of the manipulator system 1. Each surgical instrument 6 includes an insert 7 and a driven unit 15. The insert 7 is attached to a driven unit 15 and is inserted into the body of patient. The driven unit 15 is connected to a drive unit 22. One or more of the surgical instruments 6 have a high-frequency treatment instrument 6A for performing a high-frequency treatment. The high-frequency treatment instrument 6A is connected to a high-frequency power supply 60 that can be operated by a foot switch 61 for energization with a high-frequency current. The insert 7 is shaped like an elongated shank. When the insert 7 is in use, one end that is on a side of the treatment unit 8 is directed toward the body of the patient. For clarity purpose, for indicating relative axial positions on the insert 7, those closer to the treatment unit 8 is referred to as those on a distal-end side, whereas those closer to the drive unit 22 is referred to as those on a proximal-end side, unless otherwise specified. The insert 7 includes the treatment unit 8 disposed on the distal-end side to be directed toward the patient and an elongate member 10 coupled to the treatment unit 8. As depicted in FIG. 2, the treatment unit 8 includes electrodes 9 for making an incision in a tissue of the patient. For example, the electrodes 9 of the high-frequency treatment instrument 6A are capable of making an incision in a tissue when supplied with a high-frequency current from the high-frequency power supply 60. The elongated member 10 includes a joint 11 connected to the treatment unit 8 and a flexible tube 12 connected to the joint 11. In response to the transmission of drive power produced by the drive unit 22, the joint 11 operates to change the orientation of the treatment unit 8 with respect to the distal end of the flexible tube 12. A plurality of joints 11 are connected to a pulley 18 of the driven unit 15 through respective wires (W). Although in FIG. 2 one single joint 11 is illustrated, but one of ordinary skill in the art would appreciate that a plurality of joints 11 may be provided. According to the present embodiment, the elongated member 10 is illustrated as having the flexible tube 12, however, depending on the construction and the intended use, a hard tube may be used as well. The flexible tube 12 is a soft tubular member having openings at respective distal and proximal ends. The wire (w) for transmitting drive power from the drive unit 22 to the joint 11 is inserted in the flexible tube 12.

Figure 3:
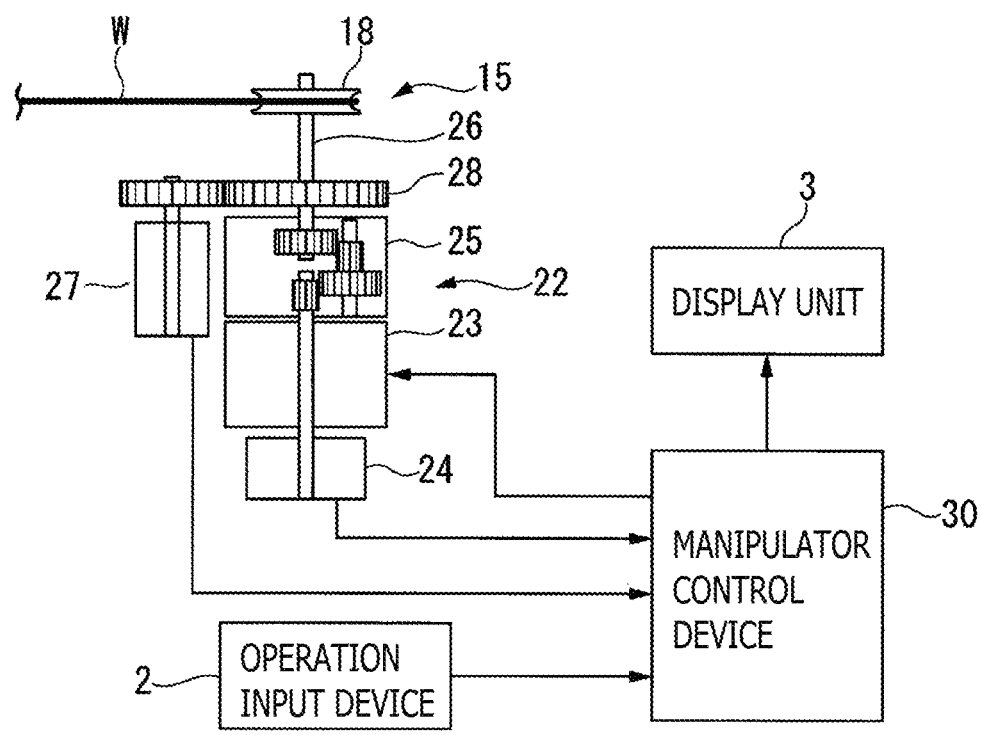
FIG. 3 is a diagram depicting internal structures of a drive unit and a driven unit of the manipulator system.

FIG. 3 is a diagram depicting internal structures of the drive unit 22 and the driven unit 15 of the manipulator system 1. The driven unit 15 includes a transmitted member or pulley 18, that is coupled to an output shaft 26 of the drive unit 22 and angularly rotatable by drive power transmitted from the drive unit 22. The pulley 18 has a groove defined in an outer circumferential surface thereof. The wire (w) extends from the proximal end of the flexible tube 12 and the wire (w) is trained in the outer circumferential surface. Drive power produced by the drive unit 22 is transmitted to the pulley 18. The drive power that is transmitted to the pulley 18 is transmitted to the wire (w). Therefore, depending on the operation of the drive unit 22, the wire (w) is advanced or retracted longitudinally in the flexible tube 12, transmitting the drive power produced by the drive unit 22 to the joint 11 as depicted in FIG. 2. The manipulator system 1 includes movable arms 21 for adjusting the positions and orientations of the surgical instruments 6. The arms 21 support the respective drive units 22. The drive unit 22 includes an electric motor 23, a drive unit encoder 24, a speed reducer mechanism 25, the output shaft 26, and a driven unit encoder 27. The electric motor 23 used as a power source electrically connected to the manipulator control device 30. The drive unit encoder 24 is connected to the rotational shaft of the electric motor 23. The speed reducer mechanism 25 is connected to the rotational shaft of the electric motor 23. The output shaft 26 is mounted on the speed reducer mechanism 25. The driven unit encoder 27 is indirectly connected to the output shaft 26 via a gear 28 and being capable to actuate by drive power transmitted from a gear 28 of the drive unit 22.

The electric motor 23 is electrically connected to the manipulator control device 30. The electric motor 23 used as a drive power source producing drive power for actuating the surgical instrument 6. The drive unit encoder 24 used as a sensor or a first sensor, for detecting an operation quantity of the drive unit 22. The drive unit encoder 24 generates a pulse signal, or a first detected value, in tandem with an angular displacement of the rotational shaft of the electric motor 23. The electric motor 23 may be a servomotor or the like including the drive unit encoder 24 for detecting an operation quantity of the electric motor 23. The driven unit encoder 27 used as a sensor or a second sensor, for detecting an operation quantity of the drive unit 22 at a site different from the drive unit encoder 24. The driven unit encoder 27 detects an operation quantity of a portion of a power transfer path from the drive unit 22 to the surgical instrument 6. For example, the portion of a power transfer path is the output shaft 26 of the speed reducer mechanism 25 in the present embodiment. The driven unit encoder 27 is connected to the output shaft 26 through a gear 28 mounted on the output shaft 26 of the speed reducer mechanism 25. The driven unit encoder 27 generates a pulse signal, or a second detected value, in tandem with an angular displacement of the output shaft 26.

Figure 4:
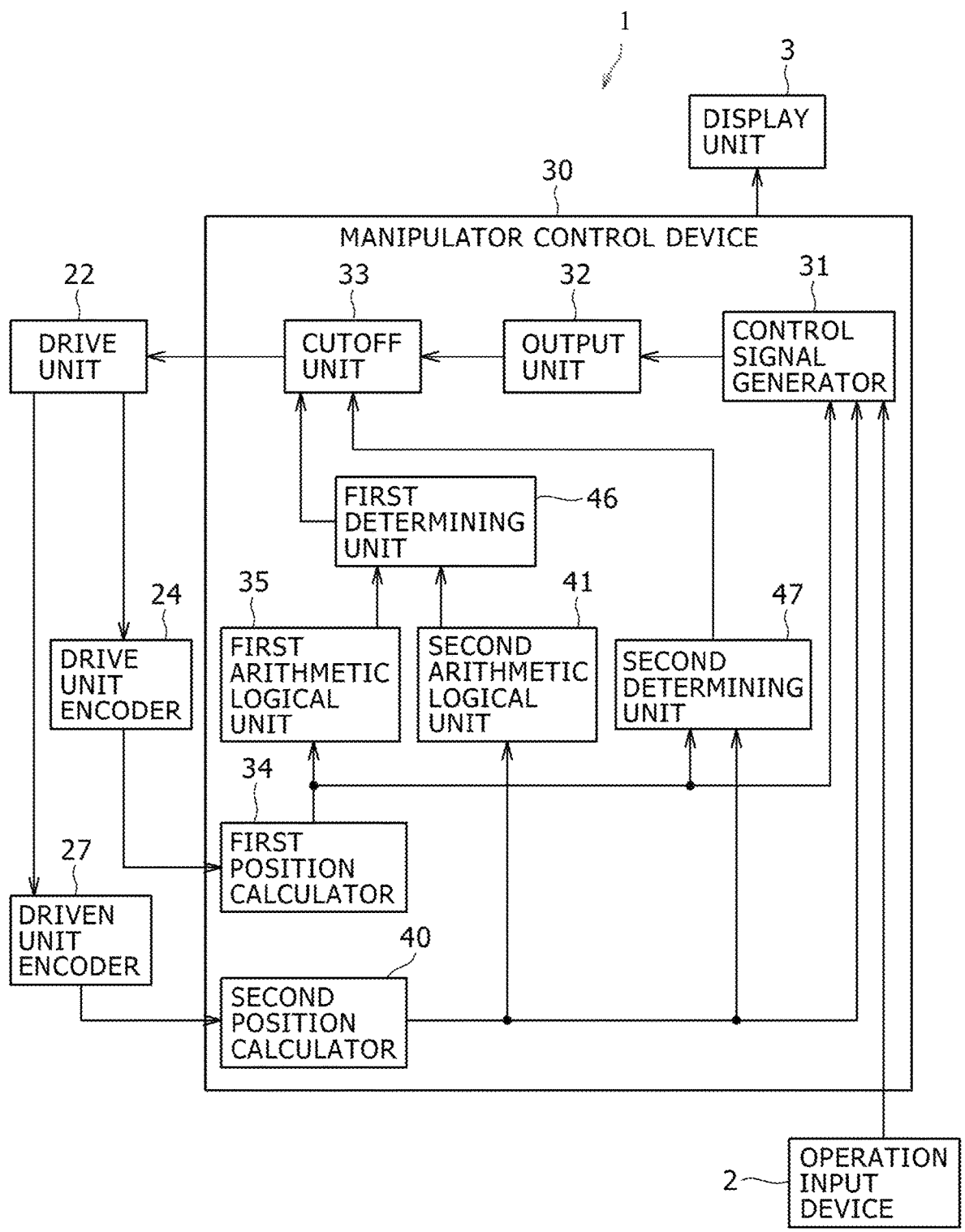
FIG. 4 is a block diagram depicting a manipulator control device of the manipulator system.

FIG. 4 is a block diagram depicting the manipulator control device 30 of the manipulator system 1. The manipulator control device 30 includes a control signal generator 31, an output unit 32, a cutoff unit 33, a first position calculator 34, a first arithmetic logic unit 35, a second position calculator 40, a second arithmetic logic unit 41, a first determining unit 46, and a second determining unit 47. The control signal generator or a first processor 31 is connected to the operation input device 2. The output unit or a driver 32, is connected to the control signal generator 31. The cutoff unit or a relay 33, is connected to the output unit 32. The first position calculator or a second processor 34 is connected to the drive unit encoder 24. The first arithmetic logic unit or a third processor 35 is connected to the first position calculator 34. The second position calculator or a fourth processor 40, is connected to the driven unit encoder 27. The second arithmetic logic unit or a fifth processor 41 is connected to the second position calculator 40. The first determining unit a sixth processor 46 or is connected to the first arithmetic logic unit 35 and the second arithmetic logic unit 41. The second determining unit or a seventh processor 47 is connected to the first position calculator 34 and the second position calculator 40. All of the processors such as first through seventh processors may be constructed as programmable devices such as CPUs, FPGAs, or the like, or devices such as ASICs. All of the processors disclosed herein may be constructed all in one device or may be constructed as respective individual devices. Further alternatively, the first through seventh processors may be divided into groups and/or devices may be assigned to those groups such that, for example, the first processor and seventh processor are constructed as one CPU and the second processor through sixth processor as FPGAs.

An operation signal input is output from the operation input device 2 to the manipulator control device 30. The control signal generator 31 receives the operation signal input. The control signal generator 31 generates control signals for moving the manipulator 5 or the surgical instruments 6. The control signal generator 31 is connected to the first position calculator 34 and the second position calculator 40. Information of drive quantities of the drive unit 22 are calculated by the first position calculator 34 and the second position calculator 40. The control signal generator 31 receives information on the drive quantities input thereto. The control signal generator 31 performs a feedback control process based on the information of the drive quantities of the drive unit 22 that are calculated by the first position calculator 34 and/or the second position calculator 40. The control signal generator 31 outputs the generated control signals to the output unit 32. The output unit 32 receives the control signals input thereto that are output from the control signal generator 31, and calculates drive signals for actuating the drive unit 22 based on the control signals. The output unit 32 outputs the generated drive signals to the cutoff unit 33. The cutoff unit or a relay 33 switches between an ON state and an OFF state according to the determined results from the first determining unit 46 and the second determining unit 47. In ON state, the cutoff unit 33 outputs the drive signals output from the output unit 32 to the electric motor 23 of the drive unit 22. In the OFF state, the cutoff unit 33 cuts off the drive signals output from the output unit 32 so that they will not be output to the electric motor 23 of the drive unit 22. Immediately after the cutoff unit 33 is activated until a cutoff signal, or a first cutoff signal or a second cutoff signal, is output from the first determining unit 46 and the second determining unit 47, the drive signals from the output unit 32 can be output to the electric motor 23 of the drive unit 22.

The first position calculator 34 receives the pulse signal generated by the drive unit encoder 24. The first position calculator 34 integrates pulse signals from the drive unit encoder 24 and generates a count value. The first position calculator 34 calculates a value corresponding to an operation quantity of the electric motor 23, hereinafter referred to as a first operation quantity Ca, based on an initial count value (0) and a latest count value. The first operation quantity Ca is output to the first arithmetic logic unit 35, the second determining unit 47, and the control signal generator 31. The second position calculator 40 receives the pulse signal generated by the driven unit encoder 27. The second position calculator 40 integrates pulse signals from the driven unit encoder 27 and generates a count value. The second position calculator 40 calculates a value corresponding to an operation quantity of the electric motor 23, hereinafter referred to as a second operation quantity Cb, based on an initial count value (0) and a latest count value.

The second operation quantity Cb is output to the second arithmetic logic unit 41, the second determining unit 47, and the control signal generator 31. The second determining unit 47 compares the absolute value of the difference between the output Ca from the first position calculator and the output Cb from the second position calculator with a predetermined threshold value, hereinafter referred to as a third threshold value R3, to determine a failure. If the second determining unit 47 determines that there is a failure, then the second determining unit 47 outputs a cutoff signal, or a second cutoff signal. The third threshold value R3 is a positive value that is larger than an allowable error between the first operation quantity Ca and the second operation quantity Cb, and that is as close to 0 as possible. The first determining unit 46 determines whether the drive unit encoder 24 is operating normally or not based on output values of the first arithmetic logic unit 35 and the second arithmetic logic unit 41, i.e., performs a failure determination, and outputs a cutoff signal, or a first cutoff signal, if it determines that there is a failure.

Figure 5:
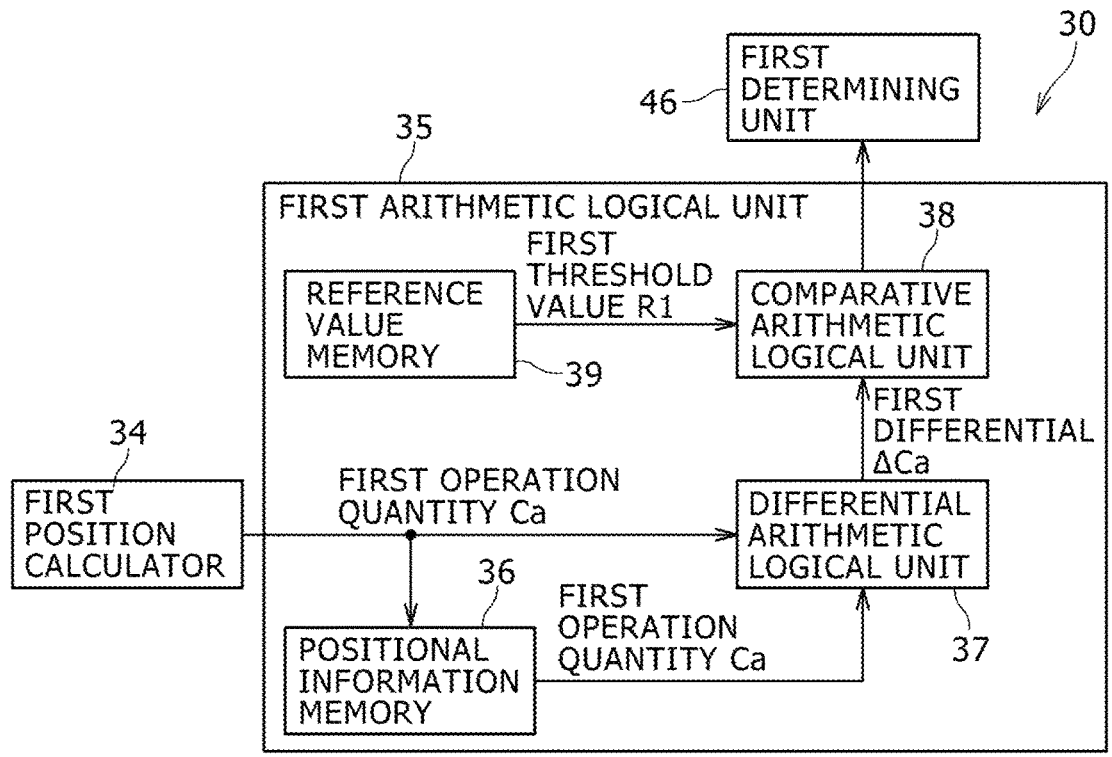
FIG. 5 is a block diagram depicting a first arithmetic logic unit of the manipulator control device.

FIG. 5 is a block diagram depicting the first arithmetic logic unit 35 of the manipulator control device 30. The first operation quantity Ca output from the first position calculator 34 is input to the first arithmetic logic unit 35. The first arithmetic logic unit 35 includes a position information memory 36, a difference arithmetic logic unit 37, a reference value memory 39, and a comparative arithmetic logic unit 38. The position information memory 36 acquires first operation quantities Ca at predetermined time intervals from the first position calculator 34 and storing the acquired first operation quantities Ca. The difference arithmetic logic unit 37 calculates and execute difference between an output from the first position calculator 34 and an output from the position information memory 36. The reference value memory 39 stores a predetermined reference value, hereinafter referred to as a first threshold value R1. The comparative arithmetic logic unit 38 compares and outputs an output from the reference value memory 39. A first operation quantity Ca acquired at certain time n is expressed as Ca(n). Ca(n) is input to the position information memory 36 and the difference arithmetic logic unit 37 at the same time. The position information memory 36 is capable of storing at least (i) a latest first operation quantity Ca(n) at the time the first operation quantity Ca is acquired and (ii) a first operation quantity Ca(n−1) acquired immediately before the latest first operation quantity Ca(n). At the time Ca(n) is input to the position information memory 36, the position information memory 36 outputs Ca(n−1) that has been input and stored immediately before Ca(n). The difference arithmetic logic unit 37 calculates the difference between Ca(n) from the first position calculator 34 and Ca(n−1) from the positional information memory 36, hereinafter referred to as a first differential ΔCa, or ΔCa(n) if the difference is of a value at time n. The first differential ΔCa is of a value representing an operation quantity of the drive unit 22 per unit time based on the pulse signal from the drive unit encoder 24. The difference arithmetic logic unit 37 outputs the first difference ΔCa to the comparative arithmetic logic unit 38. The comparative arithmetic logic unit 38 reads the first threshold value R1 from the reference value memory 39 and compares the absolute value of the first difference ΔCa with the first threshold value R1. The first threshold value R1 is a positive value that is larger than an error which can occur to the first difference ΔCa when the mechanism of the drive unit 22 operates normally, and that is as close to 0 as possible. The first threshold value R1 is determined based on the resolution of the drive unit encoder 24 and drive power transfer characteristics such as a speed reduction ratio, etc. from the electric motor 23 to the drive unit encoder 24.

Figure 6:
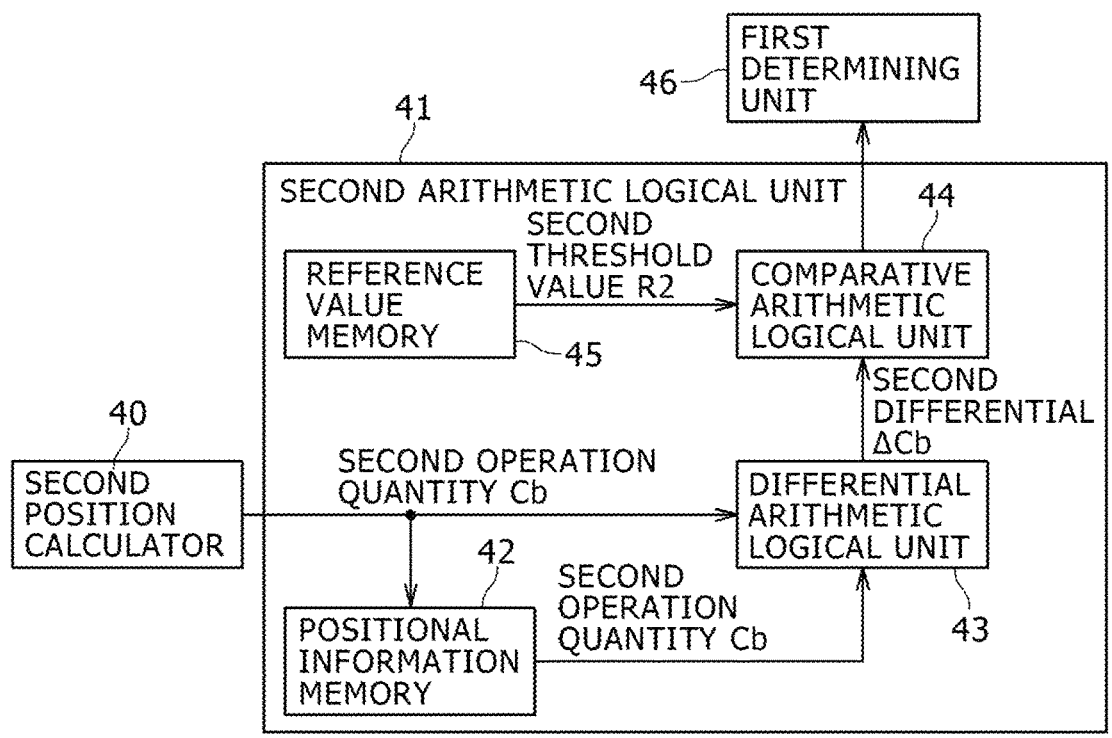
FIG. 6 is a block diagram depicting a second arithmetic logic unit of the manipulator control device.

FIG. 6 is a block diagram depicting the second arithmetic logic unit 41 of the manipulator control device 30. The second operation quantity Cb output from the second position calculator 40 is input to the second arithmetic logic unit 41. The second arithmetic logic unit 41 includes a position information memory 42, a differential arithmetic logic unit 43, a reference value memory 45, and a comparative arithmetic logic unit 44. The position information memory 42 acquires second operation quantities Cb at predetermined time intervals from the second position calculator 40 and stores the acquired second operation quantities Cb. The difference arithmetic logic unit 43 calculates and outputs a difference between an output from the second position calculator and an output from the position information memory 42. The reference value memory 45 stores a predetermined reference value, hereinafter referred to as a second threshold value R2. The comparative arithmetic logic unit 44 compares and outputs an output from the difference arithmetic logic unit 43 and an output from the reference value memory 45. A second operation quantity Cb acquired at certain time n is expressed as Cb(n). Cb(n) is input to the position information memory 42 and the difference arithmetic logic unit 43 at the same time. The position information memory 42 is capable of storing at least (i) a latest second operation quantity Cb(n) at the time the second operation quantity Cb is acquired and (ii) a second operation quantity Cb(n−1) acquired immediately before the latest second operation quantity Cb(n). At the time Cb(n) is input to the position information memory 42, the position information memory 42 outputs Cb(n−1) that has been input and stored immediately before the latest second operation quantity Cb(n). The time at which the second arithmetic logic unit 41 acquires a second operation quantity Cb(n) is synchronous with the time at which the first arithmetic logic unit 35 acquires a first operation quantity Ca(n). The difference arithmetic logic unit 43 calculates the difference between Cb(n) from the second position calculator 40 and Cb(n−1) from the position information memory 42, hereinafter referred to as a second difference ΔCb, or ΔCb(n) if the difference is of a value at time (n). The second difference ΔCb is of a value representing an operation quantity of the drive unit 22 per unit time based on the pulse signal from the driven unit encoder 27. The difference arithmetic logic unit 43 outputs the second difference ΔCb to the comparative arithmetic logic unit 44.

Figure 7:
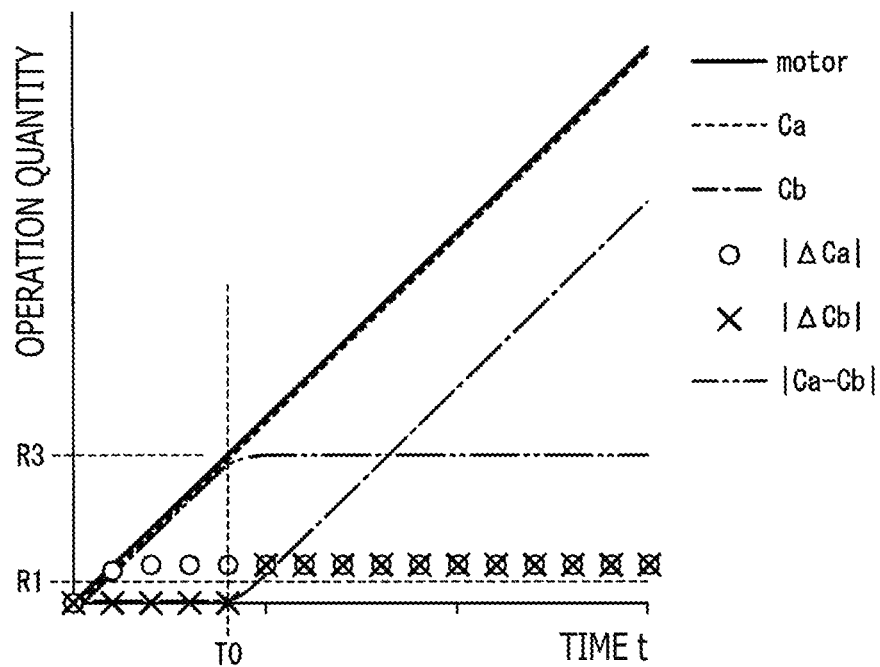
FIG. 7 is a graph depicting the principle of a failure determination by a first determining unit of the manipulator control device and the drive unit is in the state of operating normally.
Figure 8:
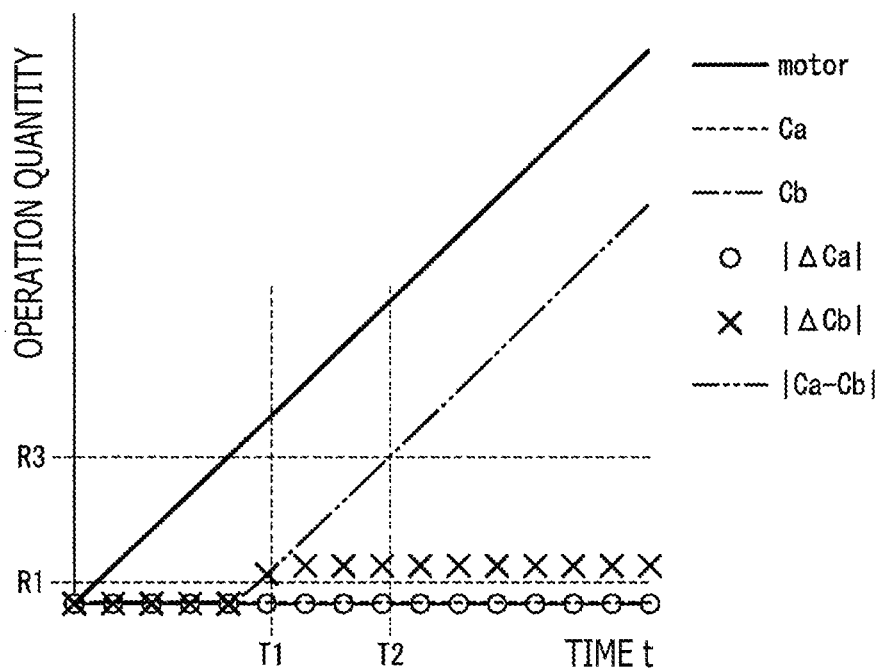
FIG. 8 is a graph depicting the principle of the failure determination by the first determining unit of the manipulator control device and one of sensors fails at the time a drive unit starts operating.
Figure 9:
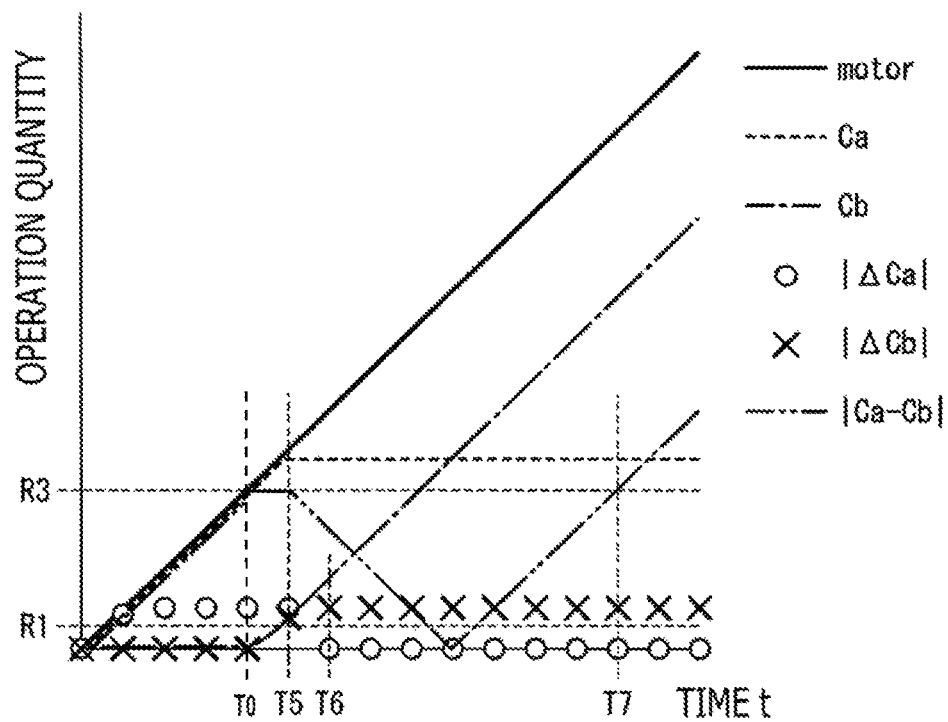
FIG. 9 is a graph depicting the principle of the failure determination by the first determining unit of the manipulator control device and one of sensors fails while a drive unit is operating.

The comparative arithmetic logic unit 44 reads the second threshold value R2 from the reference value memory 45 and compares the absolute value of the second difference ΔCb with the second threshold value R2. The second threshold value R2 is a positive value that is larger than an error which can occur to the second difference ΔCb when the mechanism of the drive unit 22 operates normally, and that is as close to 0 as possible. The second threshold value R2 is determined based on the resolution of the driven unit encoder 27 and drive power transfer characteristics such as a speed reduction ratio, etc. from the electric motor 23 to the driven unit encoder 27. If the absolute value of the first difference ΔCa is smaller than the first threshold value R1 and the absolute value of the second difference ΔCb exceeds the second threshold value R2, then the first determining unit 46 outputs a first cutoff signal to the cutoff unit 33. The first cutoff signal switches the cutoff unit 33 to the OFF state to cut off a drive current. The first cutoff signal is a shutoff signal for cutting off a drive signal to the electric motor 23. The principle of a failure determination by the first determining unit 46 will be described hereinafter with reference to FIGS. 7 through 9. FIGS. 7 through 9 represent graphs depicting time-depending changes in (i) the operation quantity of the electric motor upon operation of the manipulator control device, (ii) the first and second operation quantities Ca and Cb, (iii) the absolute value |Ca−Cb| of the difference between the first and second operation quantities, and (iV) the absolute values |ΔCa|, |ΔCb| of the first and second differences.

According to the present embodiment, as depicted in FIG. 3, (i) a power transfer path from the electric motor 23 to the drive unit encoder 24 and (ii) a power transfer path from the electric motor 23 to the driven unit encoder 27 are power transfer paths in which they are mechanically coupled to each other and operate in interlocked relation. The power transfer path from the electric motor 23 to the drive unit encoder 24 and the power transfer path from the electric motor 23 to the driven unit encoder 27 have respective inherent backlashes. Since the drive unit encoder 24 is directly mounted on the shaft of the electric motor 23, the backlash is so small that it can be ignored. On the other hand, since the driven unit encoder 27 receives power from the electric motor 23 through the speed reducer mechanism 25 and the gear 28, the backlash is noticeable. When the electric motor 23 is operating in one direction beyond a dead zone due to the backlashes after it has started to operate, the drive unit encoder 24 and the driven unit encoder 27 are interlocked with each other highly accurately. The principle of a failure determination by the second determining unit 47 will be described below with reference to FIGS. 7 through 9. FIG. 7 depicts changes in the values in case the drive unit 22, i.e., the drive unit encoder 24 and the driven unit encoder 27, is operating normally. The first operation quantity Ca that is calculated based on the output from the drive unit encoder 24 represents essentially the same as the operation quantity of the electric motor 23 because there is almost no backlash. In the graph depicted in FIG. 7, a curve representing the operation quantity of the electric motor 23 and a curve representing the first operation quantity Ca are illustrated as essentially overlapping each other. On the other hand, the second operation quantity Cb that is calculated based on the output from the driven unit encoder 27 starts increasing at a time that lags by T0 behind the time at which the electric motor 23 starts to operate due to the backlashes, and then is linked with the operation of the electric motor 23. The absolute value |Ca−Cb| of the difference between the first operation quantity and the second operation quantity, which is calculated by the second determining unit 47, increases in unison with Ca as Ca increases until T0 and Cb remains 0. After T0, Cb increases similarly to Ca, and hence |Ca−Cb| does not increase anymore, or |Ca−Cb| remains essentially constant. The value |Ca−Cb| at T0 defines as the third threshold value R3 referred to above. If either the drive unit encoder 24 or the driven unit encoder 27 fails and outputs no pulses, then since the difference between Ca and Cb becomes larger, the failure can be detected. On the other hand, if |Ca−Cb| increases but does not exceed R3, then the backlashes may be responsible though there may be a possible failure. If the electric motor 23 operates repeatedly in normal and reverse directions, then |Ca−Cb| is of a value other than zero (0), and the value is equal to or smaller than R3, under the influence of the backlashes. The drive unit encoder 24 and the driven unit encoder 27 operate normally and |Ca−Cb| is essentially constant at R3. Consequently, in order to prevent an erroneous determination, a threshold value larger than R3 in FIG. 7 has to be use.

FIG. 8 depicts changes in the values in case the drive unit encoder 24 fails at the time the drive unit 22 starts operating. Since the drive unit encoder 24 fails and outputs no pulses, the first operation quantity Ca that is calculated based on the output of the drive unit encoder 24 remains zero (0). On the other hand, the second operation quantity Cb that is calculated based on the output of the driven unit encoder 27 starts increasing at a time that lags behind the time at which the electric motor 23 starts to operate, and then is linked with the operation of the electric motor 23, in the same manner as if the drive unit encoder 24 operates normally. The |Ca−Cb| remains zero (0) as both Ca and Cb are zero (0) up to a dead zone T0, not depicted, due to the backlashes. After T0, Cb increases but Ca remains zero (0), so that |Ca−Cb|=Cb. In the graph depicted in FIG. 8, a curve representing the |Ca−Cb| and a curve representing Cb are illustrated as overlapping each other. The |Ca−Cb| continues to increase until it exceeds R3, whereupon the occurrence of a failure is detected. The determination in this case requires a time up to T2 until a failure that has occurred is detected.

FIG. 9 depicts changes in the values in case the drive unit encoder 24 fails at time T5 (>T0) while the drive unit 22 is operating. Until T5, the drive unit 22 operates in the same manner as if it operates normally, and the |Ca−Cb| continues to increase until T0, not depicted, and then is of a constant value after T0. Thereafter, when the drive unit encoder 24 stops outputting pulses at T5, Ca stops increasing, and only Cb increases. If the |Ca−Cb| that has become large, then starts decreasing. Cb continues to increase to a value that is the same as Ca, whereupon the |Ca−Cb| changes to increase. A failure of the drive unit encoder 24 is determined when the |Ca−Cb| subsequently exceeds R3. The determination in this case requires a time T7-T5 until a failure that has occurred is detected. The second determining unit 47 is thus able to detect failures of both the drive unit encoder 24 and the driven unit encoder 27, though it takes time until the failures are detected. The second determining unit 47 does not output a second cutoff signal if the absolute value of the difference between the first operation quantity Ca and the second operation quantity Cb is equal to or smaller than the third threshold value R3. The principle of a failure determination by the first determining unit 46 will be described hereinafter with reference to FIGS. 7 through 9.

FIG. 7 depicts changes in the values in case the drive unit 22 is operating normally, as described hereinbefore. Attention is drawn to the absolute value |ΔCa|, indicated by "○" in FIG. 7, of the first difference ΔCa and the absolute value |ΔCb|, indicated by "x" in FIG. 7, of the second difference ΔCb. While the drive unit 22 is operating normally, |ΔCa|takes a positive value as Ca increases and remains essentially the same value if the drive unit 22 is operating at a constant speed. Similarly, |ΔCb| takes a positive value as Cb increases. A value which is approximately one-half of Ca at the time the drive unit 22 is operating at an expected speed is set as the first threshold value R1. In case the drive unit 22 is operating normally, if |ΔCa| is smaller than R1, the electric motor 23 is de-energized. The second threshold value R2 is similarly set for ΔCb|. In this example, R2=R1. However, if the drive unit encoder 24 and the driven unit encoder 27 have different resolutions and rotational speeds, then it is desirable to determine R1 and R2 under respective conditions. If |ΔCb| is smaller than R1, then either the electric motor 23 is de-energized or the electric motor 23 is energized but the driven unit encoder 27 is not yet rotated due to the backlash. Conversely, if |ΔCb| is larger than R1, then the electric motor 23 is rotating. The fact that |ΔCa| is smaller than R1 at the time the drive unit 22 is supplied with electric power indicates that some failure has occurred. If |ΔCb| is larger than R1 at this time, then since it indicates that the electric motor 23 is rotated, the drive unit encoder 24 that is associated with |ΔCa| is found as failing.

FIG. 8 depicts changes in the values in case the drive unit encoder 24 fails at the time the drive unit 22 starts operating. Since the drive unit encoder 24 fails and outputs no pulses in this case, the (i) first operation quantity Ca that is calculated based on the output of the drive unit encoder 24 and (ii) |ΔCa|remain zero (0). On the other hand, the second operation quantity Cb that is calculated based on the output of the driven unit encoder 27 starts increasing at a time that lags behind the time at which the electric motor 23 starts to operate due to the backlash in the same manner as if the drive unit encoder 24 operates normally. Then, the second operation quantity Cb increases in interlocked relation to the operation of the electric motor 23. |ΔCb| exceeds R1 at T1 when the second operation quantity Cb starts to increase.

In this case, |ΔCa| and |ΔCb| are related to the threshold values as indicated by the following equations (1) and (2):

$$|\Delta Ca| < R1 \qquad \text{(Equation 1)}$$

$$|\Delta Cb| > R2(=R1) \qquad \text{(Equation 2)}$$

When the relationships indicated by the above equations (1) and (2) are satisfied, the first determining unit 46 operates as described above to determine a failure and the first determining unit 46 outputs a first cutoff signal. The determination in this case makes it possible to detect a failure at time T1 after it has occurred, earlier than T2 with respect to the second determining unit 47 as described above, and hence can stop malfunction due to the failure, more quickly.

FIG. 9 depicts changes in the values in case the drive unit encoder 24 fails at time T5 (>T0) while the drive unit 22 is operating. In this case, since the drive unit 22 operates in the same way as when it operates normally up to T5, |ΔC| takes a value equal to or larger than R1, and |ΔCb| is 0 up to T0, not depicted, and takes a value equal to or larger than R1 after T0. Then, if the drive unit encoder 24 stops producing pulses at T5, Ca stops increasing, and at next time T6, |ΔCa| becomes 0 and Cb continues to increase, so that |ΔCb| continues to take a value in excess of R1. As the criterion for a failure determination by the first determining unit 46 is met at this time, the drive unit encoder 24 is determined as failing. The determination in this case makes it possible to detect a failure at time T6-T5 from the occurrence of the failure, earlier than T7-T5 with respect to the second determining unit 47 as described above, and hence can stop malfunction due to the failure, more quickly. The first determining unit 46 does not output a first cutoff signal if the absolute value of the first difference ΔCa is equal to or larger than the first threshold value R1 or if the absolute value of the second difference ΔCb is equal to or smaller than the second threshold value R2. Based on the above operating principles in combination, the manipulator system 1 according to the present embodiment operates so as to cause a system shutdown in the event of a failure of the drive unit encoder 24 and the driven unit encoder 27, as follows. If the drive unit encoder 24 fails and stops outputting pulses, then since the absolute value of the first difference ΔCa is smaller than the first threshold value R1 and the absolute value of the second difference ΔCb exceeds the second threshold value R2, the criterion for a failure determination by the first determining unit 46 is met, and the first determining unit 46 outputs a first cutoff signal. |Ca−Cb| increases, and at the time |Ca−Cb| exceeds R3, the second determining unit 47 outputs a second cutoff signal to the cutoff unit 33. Since the determination by the first determining unit 46 is earlier than the determination by the second determining unit 47, the first cutoff signal is output to the cutoff unit 33 before |Ca−Cb| exceeds R3, de-energizing the electric motor 23 that serves as a power source. If the driven unit encoder 27 fails and stops outputting pulses, then since the absolute value of the first difference ΔCa is larger than the first threshold value R1 and the absolute value of the second difference ΔCb does not exceed the second threshold value R2, the criterion for a failure determination by the first determining unit 46 is not met, and the first determining unit 46 does not output a first cutoff signal. |Ca−Cb| increases, and at the time |Ca−Cb| exceeds R3, the second determining unit 47 outputs a second cutoff signal to the cutoff unit 33, de-energizing the electric motor 23 that serves as a power source.

Specific examples of setting the first threshold value R1, the second threshold value R2, and the third threshold value R3 will be described below. According to a specific example in FIG. 3, it is assumed that the resolution of the drive unit encoder 24 is 4000 pulses/revolution. The resolution of the driven unit encoder 27 is 3600 pulses/revolution. The speed reduction ratio of the speed reducer mechanism 25 is 36:1. The speed reduction ratio of the gear 28 is 1:1. The backlash between the electric motor 23 and the driven unit encoder 27, as converted into an angular displacement of the pulley 18, is 2 degrees. The backlash between the electric motor 23 and the drive unit encoder 24 is 0 degree. The lowest rotational speed of the pulley 18 at the time the drive unit 22 is operating is 3 degrees/second.

When the electric motor 23 is energized at the lowest rotational speed, the drive unit encoder 24 and the driven unit encoder 27 output pulses respectively at the following rates:

1200 pulses/second
30 pulses/second

In order to normalize them, only the count of the pulses from the driven unit encoder 27 is multiplied by 40, and the result is used as Cb. When the count is sampled at intervals of 100 milliseconds, or 0.1 second, |ΔCa|=|ΔCb|=120. This is the value of |ΔCa| or |ΔCb| at the time the electric motor 23 is rotated at the lowest rotational speed. Therefore, threshold values used to determine whether the electric motor 23 is rotated or not should be smaller than the above value. If the threshold values are 0, then since a speed irregularity or a rotation error may be detected as an error. Therefore, the threshold values are set to a value between 0 and the value at the time the electric motor 23 is rotated at the lowest rotational speed. For example, the threshold values may be set to one-half of the value at the time the electric motor 23 is rotated at the lowest rotational speed, i.e.,

R1=R2=60

In a system containing noises and errors, R1 may be set to a slightly low value as it used as an upper limit value reference and R2 may be set to a slightly high value as it used as a lower limit value reference, thereby avoiding erroneous determinations due to noises and errors.

It is possible to set R1 and R2 as follows:
R1=50
R2=70

Therefore, the first threshold value R1 should preferably be equal to or smaller than the second threshold value R2 (R1<R2). As the lowest rotational speed of the pulley 18 is 3 degrees/second, the resolution for counting Ca and Cb is 400 pulses/degree, and the backlash as a dead zone is 2 degrees, so that the third threshold value R3 may be selected as follows:

R3>800

By giving a margin of approximately 10% to the above value, the third threshold value R3 may be set as follows:

R3=900

The third threshold value R3 may include a certain margin for the purpose of preventing erroneous determinations due to noises, etc.

Figure 10:
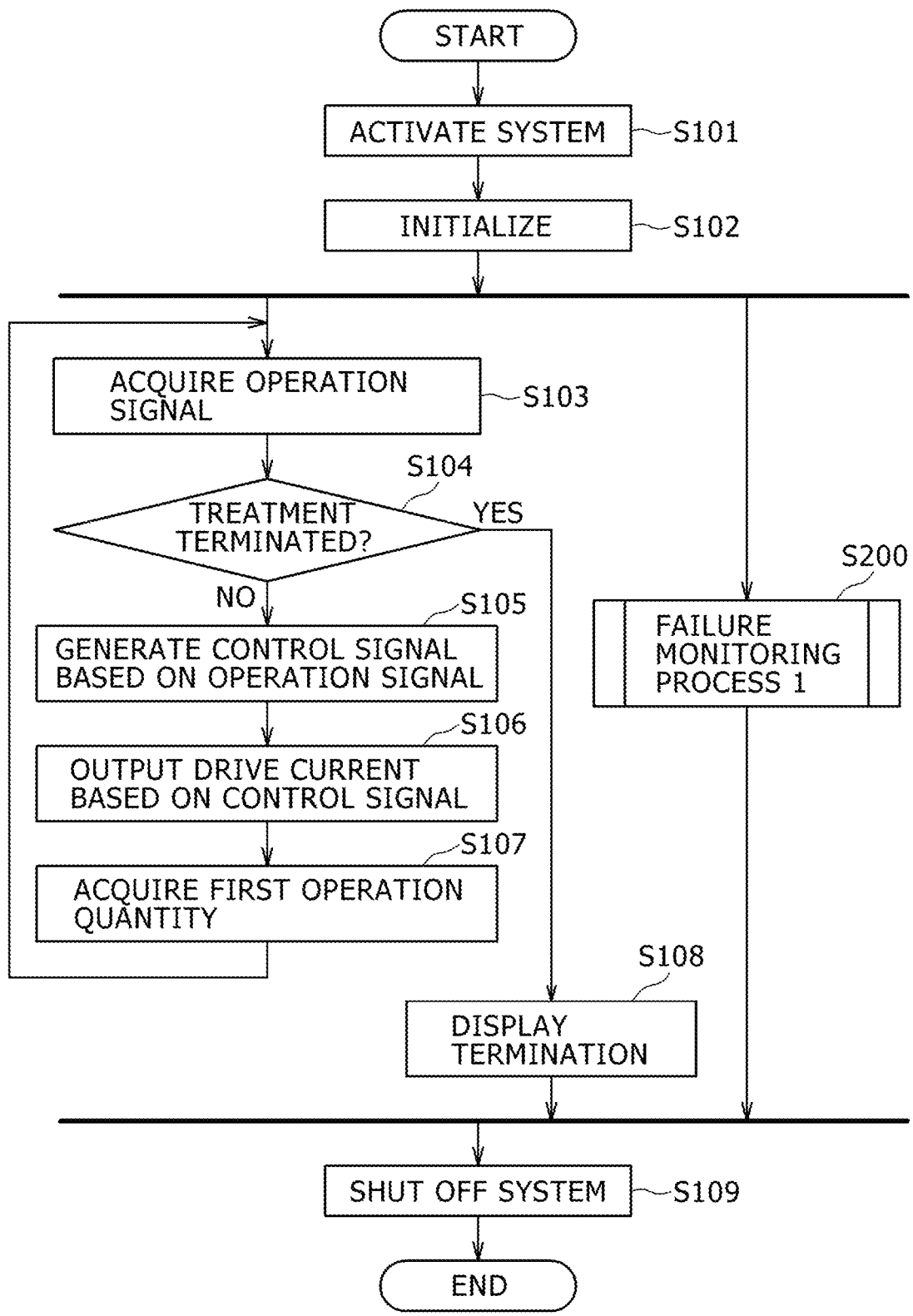
FIG. 10 is a flowchart depicting an outline of operation of the manipulator system according to the first embodiment.

Operation of the manipulator system 1 according to the present embodiment will be described hereinafter with reference to FIG. 10. FIG. 10 is a flowchart depicting an outline of operation of the manipulator system 1 according to the present embodiment. The manipulator system 1 is used with the surgical instruments 6 connected to the drive unit 22. The manipulator system 1 is activated in step S101, and the manipulator control device 30 is initialized in step S102. The drive unit 22 is moved to a preset position for initialization. When the manipulator control device 30 is initialized, the counts of pulse signals in the first position calculator 34 and the second position calculator 40 are initialized. In subsequent operation, the initialized counts represent displacement 0, and the counts increase or decrease according to pulse signals output from the drive unit encoder 24 and the driven unit encoder 27. Then, the user operates the operation unit 4 while viewing an image on the display unit 3 of the operation input device 2. The operation unit 4 outputs an operation signal in accordance with the movement of the user who operates the operation unit 4 to the manipulator control device 30. The manipulator control device 30 acquires the operation signal from the operation unit 4 in step S103. The manipulator control device 30 determines whether the user has input an instruction to terminate the treatment using the operation input device 2 or not. If no terminating instruction is input as indicated by "No" in step S104, then the control signal generator 31 generates a control signal based on the operation signal and a first operation quantity in step S105. In the manipulator control device 30, the output unit 32 outputs a drive signal according to the control signal to the cutoff unit 33. The cutoff unit 33 outputs the drive signal to the electric motor 23 of the drive unit 22 in step S106. The electric motor 23 of the drive unit 22 is now energized according to the operation on the operation unit 4. In response to the drive signal from the cutoff unit 33, the electric motor 23 of the drive unit 22 rotates the output shaft 26. At this time, both the drive unit encoder 24 connected to the electric motor 23 and the driven unit encoder 27 indirectly connected to the electric motor 23 through the output shaft 26 generate respective pulse signals based on the operation quantity of the electric motor 23.

Figure 11:
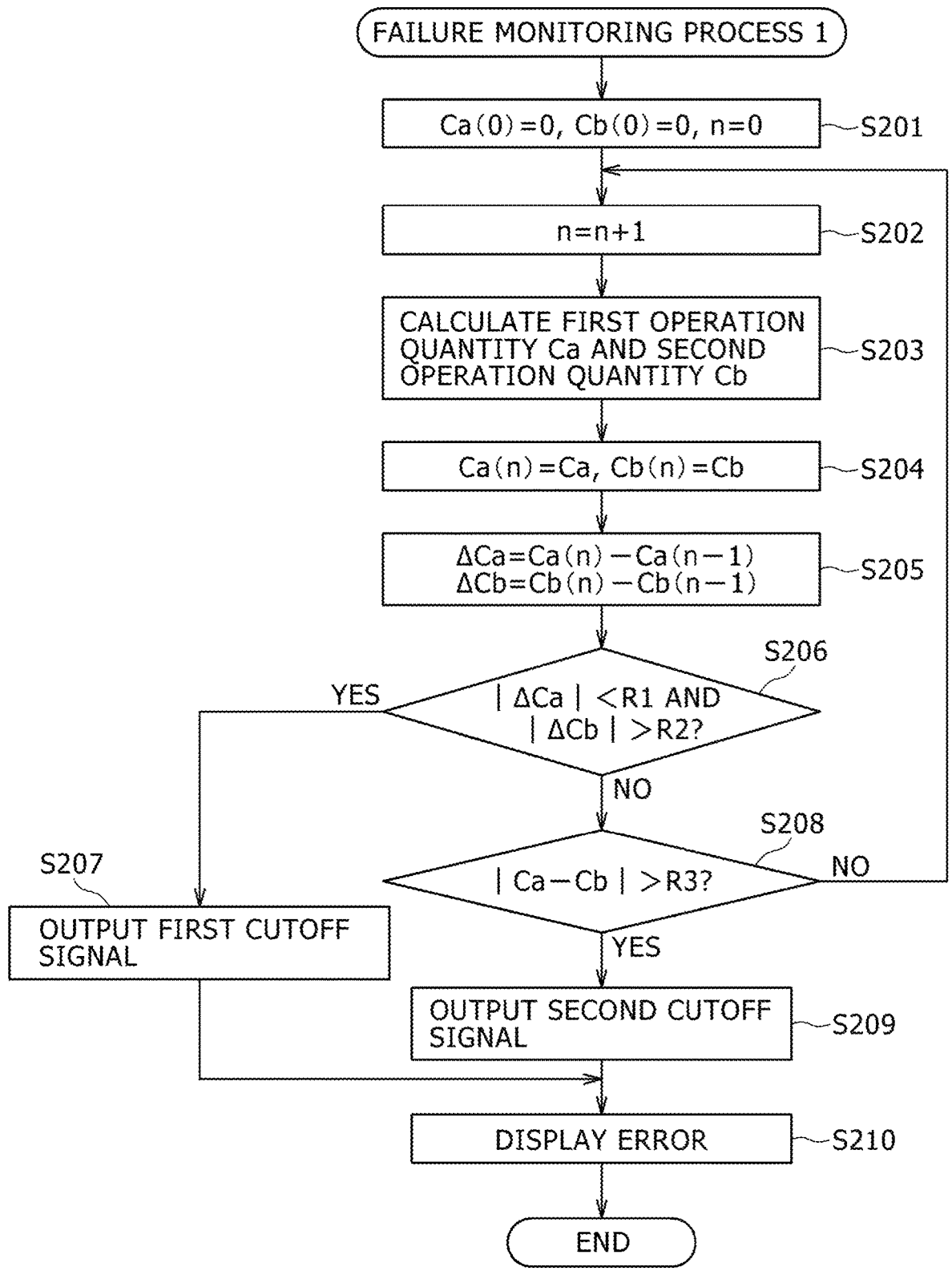
FIG. 11 is a flowchart depicting steps of operation of the failure determination by the first determining unit and a second determining unit of the manipulator system.

The first position calculator 34 calculates an operation quantity of the electric motor 23 based on the pulse signal generated by the drive unit encoder 24. The second position calculator 40 calculates an operation quantity of the electric motor 23 based on the pulse signal generated by the driven unit encoder 27. The operation quantity or a first operation quantity Ca, calculated by the first position calculator 34 is read into the control signal generator 31 and used for feedback control as information representing the present displacement of the drive unit 22. A second operation quantity Cb calculated by the second position calculator 40 may be read into the control signal generator 31 and used for feedback control or the like as information representing the present displacement of the drive unit 22. For feedback control in the control signal generator 31, either one of the first operation quantity Ca and the second operation quantity Cb may be available for use. Concurrent with its control process for actuating the drive unit 22, the manipulator control device 30 performs a monitoring step in step S200 for a failure determination for the drive unit encoder 24 and the driven unit encoder 27. The control process of the manipulator control device 30 for a failure determination will be described below with reference to a flowchart. FIG. 11 is such a flowchart depicting a flow of operation of the failure determination by the first determining unit 46 and the second determining unit 47 of the manipulator system 1. After the manipulator control device is activated and the surgical instruments 6 are mounted on the drive unit 22, the manipulator control device 30 initializes the first position calculator 34 and the second position calculator 40 in step S201. Since the first position calculator 34 and the second position calculator 40 are initialized after the surgical instruments 6 have been mounted on the drive unit 22, the positions and orientations of the surgical instruments 6 at this time represent their initial positions in the drive unit 22. Specifically, when the first position calculator 34 is initialized, the count of the pulse signal from the drive unit encoder 24 becomes zero (0). The first operation quantity Ca(n) calculated by the first position calculator 34 becomes zero (0). When the second position calculator 40 is initialized, the count of the pulse signal from the driven unit encoder 27 becomes zero (0) and the second operation quantity Cb(n) calculated by the second position calculator 40 becomes zero (0). "n" referred to above represents a variable that is reset to zero (0) when the manipulator control device 30 is initialized.

Then, the manipulator control device 30 adds 1 to (n) in step S202. After that, the first position calculator 34 calculates a first operation quantity Ca(n) and the second position calculator 40 calculates a second operation quantity Cb(n) in step S203. The first operation quantity Ca(n) is output to the first arithmetic logic unit 35 and the second determining unit 47, whereas the second operation quantity Cb(n) is output to the second arithmetic logic unit 41 and the second determining unit 47. Then, the first arithmetic logic unit 35 of the manipulator control device 30 substitutes the latest first operation quantity for the first operation quantity Ca(n) corresponding to the variable (n) in step S204. The first arithmetic logic unit 35 stores the first operation quantity Ca(n) in the position information memory 36. In step S204, furthermore, the second arithmetic logic unit 41 of the manipulator control device 30 substitutes the latest second operation quantity for the second operation quantity Cb(n) corresponding to the variable (n). The second arithmetic logic unit 41 stores the second operation quantity Cb(n) in the position information memory 42. Then, the first arithmetic logic unit 35 of the manipulator control device 30 causes the difference arithmetic logic unit 37 to calculate a first difference $\Delta Ca$ in step S205. The first difference $\Delta Ca$ represents a value calculated by subtracting a first operation quantity Ca(n−1) from the latest first operation quantity Ca(n). The first operation quantity Ca(n−1) is acquired immediately before the latest first operation quantity Ca(n). In step S205, furthermore, the second arithmetic logic unit 41 of the manipulator control device 30 causes the difference arithmetic logic unit 43 to calculate a second difference $\Delta Cb$. The second difference $\Delta Cb$ represents a value calculated by subtracting a second operation quantity Cb(n−1) from the latest second operation quantity Cb(n). The second operation quantity Cb(n−1) is acquired immediately before the latest second operation quantity Cb(n). The first difference $\Delta Ca$ and the second difference $\Delta Cb$ are output to the first determining unit 46. Then, the manipulator control device 30 causes the comparative arithmetic logic unit 38 of the first arithmetic logic unit 35 to compare the absolute value of the first difference $\Delta Ca$ and the first threshold value R1 with each other, and causes the comparative arithmetic logic unit 44 of the second arithmetic logic unit 41 to compare the absolute value of the second difference $\Delta Cb$ and the second threshold value R2 with each other. The results of comparison are output to the first determining unit 46.

Then, the first determining unit 46 combines the (i) result of comparison between the absolute value of the first difference $\Delta Ca$ and the first threshold value R1 and (ii) the result of comparison between the absolute value of the second difference $\Delta Cb$ and the second threshold value R2, to branch the processing, in step S206. If the absolute value of the first difference $\Delta Ca$ is smaller than the first threshold value R1 and the absolute value of the second difference $\Delta Cb$ is larger than the second threshold value R2 as indicated by "Yes" in step S206, then the first determining unit 46 outputs a first cutoff signal for deactivating the drive unit 22 to the cutoff unit 33 in step S207. If the absolute value of the first difference $\Delta Ca$ is equal to or larger than the first threshold value R1 or the absolute value of the second difference $\Delta Cb$ is equal to or smaller than the second threshold value R2 as indicated by "No" in step S206, then the first determining unit 46 does not output a first cutoff signal, and control goes to step S208. Then, the manipulator control device 30 causes the second determining unit 47 to compare the absolute value of the difference between the first operation quantity Ca and the second operation quantity Cb with the third threshold value R3 in step S208. If the absolute value of the difference between the first operation quantity Ca and the second operation quantity Cb is larger than the third threshold value R3 as indicated by "Yes" in step S208, then the second determining unit 47 outputs a second cutoff signal for deactivating the drive unit 22 to the cutoff unit 33 in step S209. If the absolute value of the difference between the first operation quantity Ca and the second operation quantity Cb is equal to or smaller than the third threshold value R3 as indicated by "No" in step S208, then the second determining unit 47 does not output a second cutoff signal, and control goes back to step S202. When a first cutoff signal or a second cutoff signal is output to the cutoff unit 33, the cutoff unit 33, see FIG. 4, enters the OFF state in which the drive signal is inhibited from being output to the drive unit 22. Specifically, the cutoff unit 33 of the manipulator control device 30 switches its energizing state to the ON state or the OFF state based on whether it is receiving a first cutoff signal or not, i.e., whether the first determining unit 46 determines that the absolute value of the first difference $\Delta Ca$ is smaller than the first threshold value R1 and the absolute value of the second difference $\Delta Cb$ exceeds the second threshold value R2, or not. If the cutoff unit 33 is receiving a first cutoff signal, then the cutoff unit 33 switches to the OFF state in which the current output to the drive unit 22 is cut off. Thus, when the cutoff unit 33 receives a first cutoff signal, the drive unit 22 is deactivated. If the cutoff unit 33 is not receiving a first cutoff signal, then the cutoff unit 33 switches its energizing state to the ON state or the OFF state based on whether it is receiving a second cutoff signal or not, i.e., whether the absolute value of the difference between the first operation quantity Ca and the second operation quantity Cb is in excess of the third threshold value R3 or not. If the cutoff unit 33 is receiving a second cutoff signal, then the cutoff unit 33 switches to the OFF state in which the current output to the drive unit 22 is cut off. Thus, when the cutoff unit 33 receives a second cutoff signal, the drive unit 22 is deactivated. When at least either one of first and second cutoff signals is thus output to the cutoff unit 33, the drive unit 22 is not actuated, stopping the surgical instruments 6 from operating, even if an operation is input to the operation input device 2. When the cutoff unit 33 switches to the OFF state, it may output information indicating that there is a possibility of failure and it has stopped the surgical instruments 6 from operating, to the display unit 3 or the like in step S210. Heretofore, it has been known that an encoder connected to an electric motor may be determined as failing if a signal from the encoder remains unchanged continuously for a certain period of time even when the electric motor is energized. According to such a process, the electric motor needs to operate beyond (i) an error allowed on the encoder itself and (ii) an error such as a backlash or the like in the power transfer path until the encoder is determined as failing after it has failed. Therefore, the electric motor is operated for a short period of time despite the failure of the encoder.

According to the present embodiment, in case the drive unit encoder 24 does not output a pulse signal due to a failure, the first determining unit 46 is able to detect the failure of the drive unit encoder 24 earlier than the second determining unit 47. As a result, the manipulator system 1 according to the present embodiment can quickly stop the surgical instruments 6 from operating in the event that the drive unit encoder 24 fails and is unable to output a pulse signal. Furthermore, since the second determining unit 47 is provided in the manipulator control device 30, the manipulator system 1 can stop the surgical instruments 6 from operating in case the drive unit encoder 24 outputs an inaccurate pulse signal due to a failure thereof or the driven unit encoder 27 suffers a failure. The probability that the drive unit encoder 24 and the driven unit encoder 27 which have been operating normally will fail at the same time is very low, and the probability that either one of the drive unit encoder 24 and the driven unit encoder 27 will fail earlier than the other is high. Consequently, because of the arrangement according to the present embodiment, the manipulator system 1 is capable of detecting a failure of either one of the drive unit encoder 24 and the driven unit encoder 27. Especially, the manipulator system 1 is capable of quickly detecting a failure of the drive unit encoder 24. Therefore, the manipulator system 1 can enter a safe state, i.e., a state in which the surgical instruments 6 are shut off, in the event of a failure of the power transfer to the surgical instruments 6.

Figure 12:
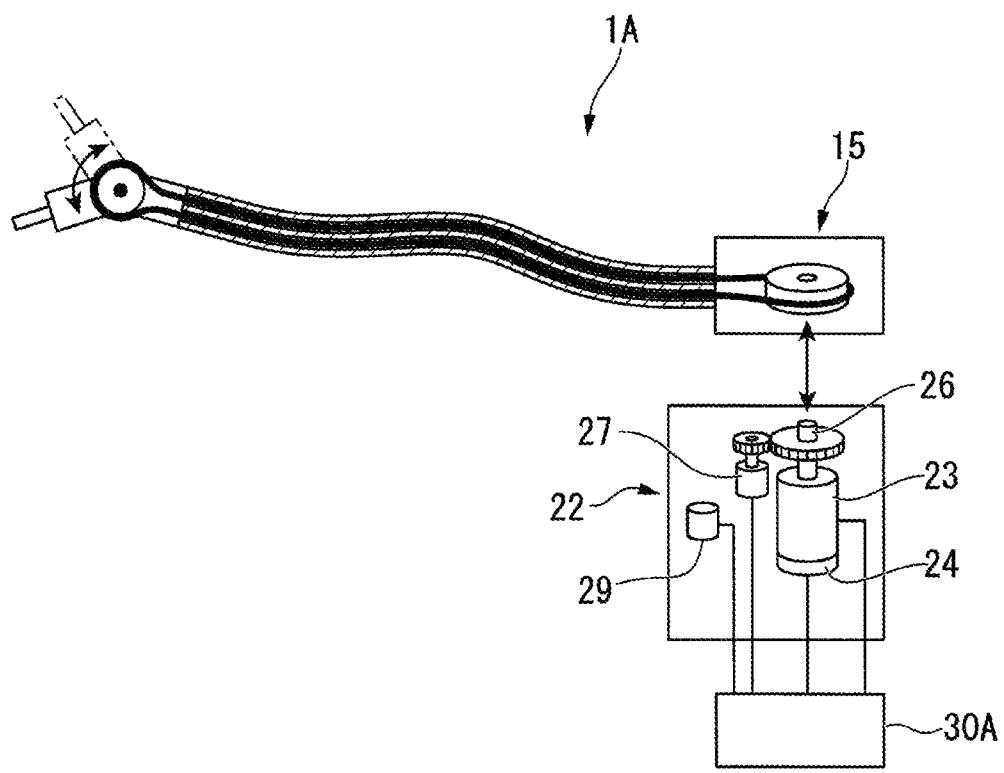
FIG. 12 is a schematic view depicting a drive unit and a driven unit of a manipulator system according to a second embodiment of the technology disclosed herein.
Figure 13:
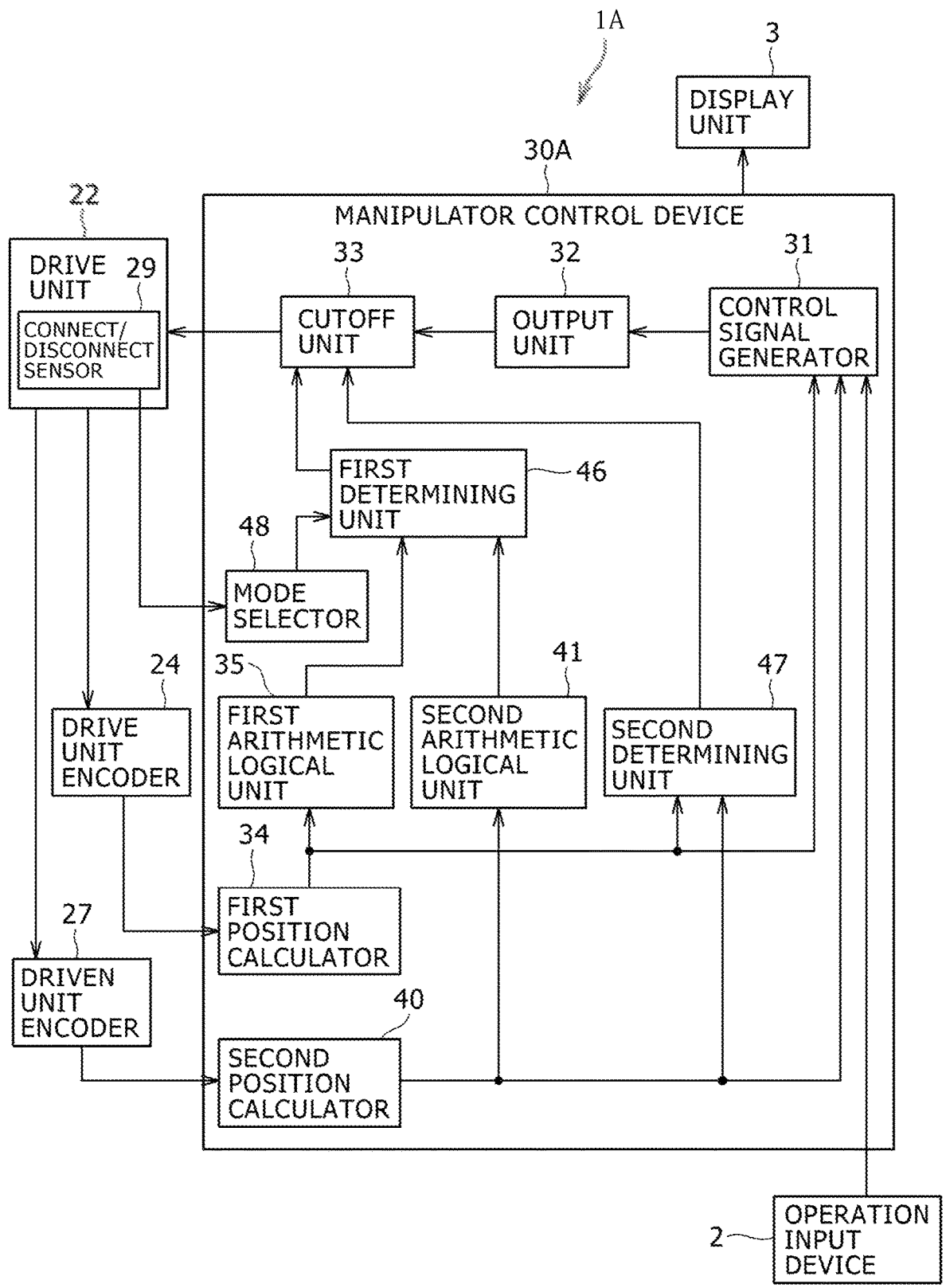
FIG. 13 is a block diagram of the manipulator system.

A second embodiment will be described hereinafter. FIG. 12 is a schematic view depicting a drive unit and a driven unit of a manipulator system 1A according to the second embodiment. FIG. 13 is a block diagram of the manipulator system 1A. The manipulator system 1A according to the present embodiment is different from the first embodiment described above in that the drive unit 22 and the driven unit 15 can be detachably attached by the user, and the manipulator system 1A includes a connect/disconnect sensor 29 for detecting whether the drive unit 22 and the driven unit are attached to one another. According the present embodiment, the connect/disconnect sensor 29 is disposed in the drive unit 22. The connect/disconnect sensor 29 is electrically connected to a manipulator control device 30A.

Figure 16:
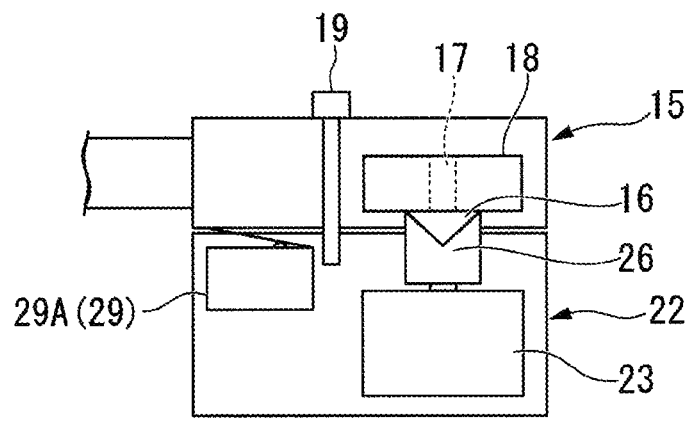
FIG. 16 is an enlarged view depicting an alternative configurational example of the drive unit and the driven unit according to the second embodiment.
Figure 17:
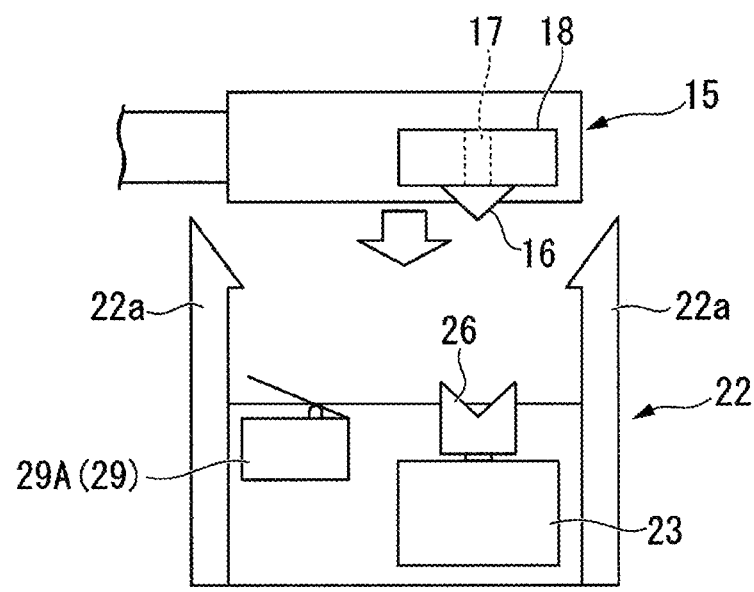
FIG. 17 is an enlarged view depicting still a further alternative configurational example of the drive unit and the driven unit according to the second embodiment.

The connect/disconnect sensor 29 has a switch that is turned on when the driven unit 15 is properly attached to the drive unit 22 and is turned off when the driven unit 15 is detached from the drive unit 22. A connect/disconnect mechanism for the drive unit 22 and the driven unit 15 may include a screw 19 depicted in FIG. 16 that couples a casing of the drive unit 22 and a casing of the driven unit 15 to each other, so that drive unit 22 and the driven unit 15 can detachably be attached to one another. The connect/disconnect sensor 29 may have a microswitch 29A disposed in the drive unit 22. When the driven unit 15 is attached to the drive unit 22 by the screw 19, the microswitch 29A is turned on by being pushed by the casing of the driven unit 15. The driven unit has a coupling 16 engageable with the output shaft 26 of the drive unit 22. The coupling 16 is connected to a rotational shaft 17 fixed to the pulley 18. The connect/disconnect mechanism for the drive unit 22 and the driven unit 15 is not limited to the mechanism described above, but may include hooks 22a on the drive unit 22 for securing the driven unit 15 to the drive unit 22, as depicted in FIG. 17. When the driven unit 15 is attached to the drive unit 22 by the hooks 22a, the microswitch 29A is turned on. The connect/disconnect sensor 29 is not limited to the switch described above, but may be any sensor insofar as it is capable of detecting whether the drive unit 22 and the driven unit 15 are attached to each other. The state of the connect/disconnect sensor 29, indicating whether it is turned on or off, is referred to the manipulator control device 30A.

The manipulator control device 30A includes a mode selector 48 in addition to the control signal generator 31, the output unit 32, the cutoff unit 33, the first position calculator 34, the first arithmetic logic unit 35, the second position calculator 40, the second arithmetic logic unit 41, the first determining unit 46, and the second determining unit 47 according to the first embodiment. The mode selector 48 selects an operation mode of the manipulator control device 30A according to a detected state from the connect/disconnect sensor 29. The mode selector 48 is connected to the connect/disconnect sensor 29 in order to be able to refer to a detected state from the connect/disconnect sensor 29. When the driven unit 15 is detached from the drive unit 22, the mode selector 48 prohibits the first determining unit 46 from operating and permits the second determining unit 47 to operate. When the driven unit 15 is attached to the drive unit 22, the mode selector 48 permits the first determining unit 46 and the second determining unit 47 to operate. According to the present embodiment, since the second determining unit 47 is always permitted to operate, the mode selector 48 is connected to the first determining unit 46 in order to selectively operate the first determining unit 46.

Figure 14:
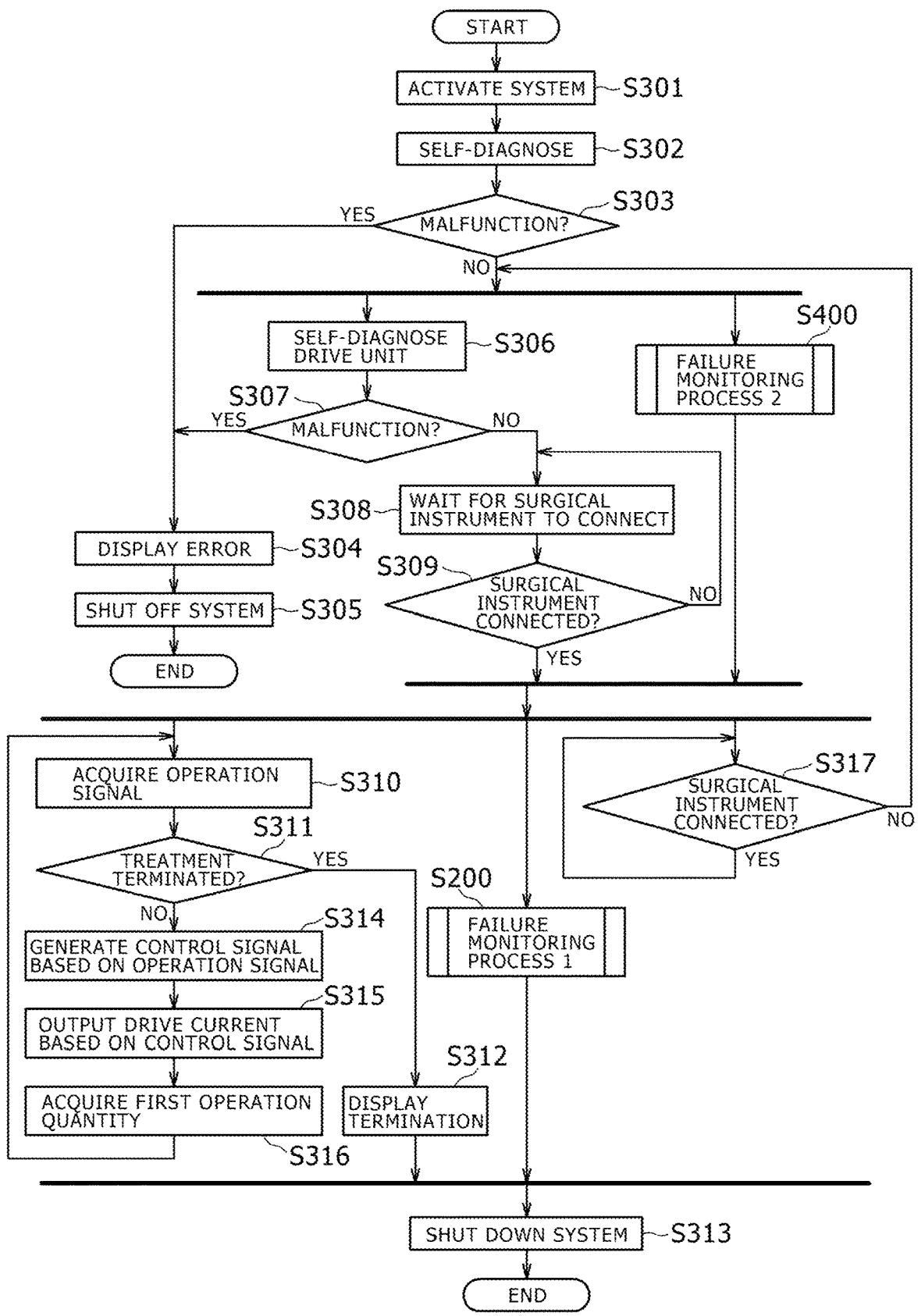
FIG. 14 is a flowchart depicting a flow of operation of the manipulator system according to the second embodiment when in use.
Figure 15:
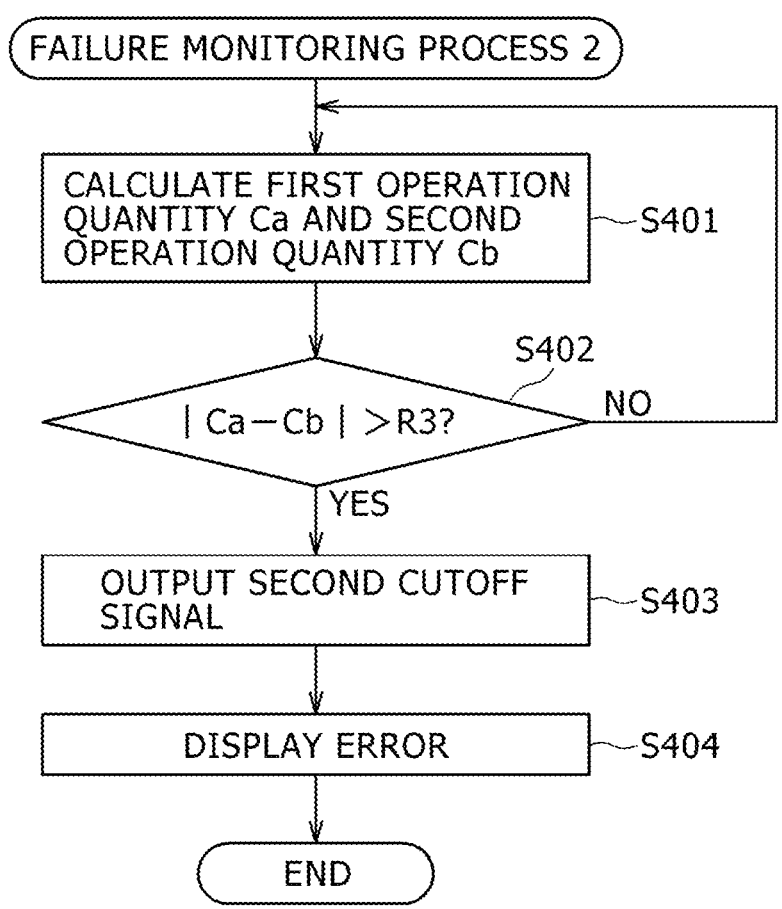
FIG. 15 is a flowchart depicting steps of operation of the manipulator system according to the second embodiment when in use.

Operation of the manipulator system 1A according to the present embodiment will be described hereinafter. FIGS. 14 and 15 are flowcharts depicting a flow of operation of the manipulator system 1A according to the present embodiment when in use. The manipulator system 1A is activated, initializing various components thereof in step S301. The manipulator control device 30A is self-diagnosed in step S302. If the manipulator control device 30A is malfunctioning as indicated by "Yes" in step S303, then an error is displayed in step S304, and the manipulator system 1A is shut off in step S305. If the manipulator control device 30A is not malfunctioning, then the manipulator system 1A enters a mode for waiting for the surgical instruments 6 to be attached. In the state for waiting for the surgical instruments 6 to be attached, the drive unit 22 is self-diagnosed in step S306. If the drive unit 22 is determined in its self-diagnosis as malfunctioning as indicated by "Yes" in step S307, then an error is displayed in step S304, and the manipulator system 1A is shut off in step S305. If the drive unit 22 is determined in its self-diagnosis as not malfunctioning as indicated by "No" in step S307, then a message is displayed on the display unit 3 for prompting the user to attach the surgical instruments 6 to the respective drive units 22. The manipulator system 1A stands by in the state for waiting for the surgical instruments 6 to be attached in step S308. Whether each of the surgical instruments 6 is attached to the corresponding drive unit 22 or not is determined based on the state of the connect/disconnect sensor 29, indicating whether it is turned on or off. If the surgical instruments 6 are determined as being attached to the respective drive units 22 as indicated by "Yes" in step S309, then the manipulator control device 30A operates in a mode for actuating the surgical instruments 6 to perform a treatment. If the surgical instruments 6 are not determined as being attached to the respective drive units 22 as indicated by "No" in step S309, then the manipulator control device 30A stands by in the state for waiting for the surgical instruments 6 to be attached in step S308. During a period of time from the self-diagnosis of the drive unit 22 until waiting for the surgical instruments 6 to be attached, since the driven unit 15 of each of the surgical instruments 6 is not attached to the drive unit 22, it is not necessary to quickly shut off the surgical instrument 6 due to a failure of the drive unit 22. During the period of time from the self-diagnosis of the drive unit 22 until waiting for the surgical instruments 6 to be attached, therefore, the manipulator control device 30A performs a monitoring process for a failure determination using only the second determining unit 47 in step S400.

After the driven unit 15 of each of the surgical instruments 6 has been attached to the drive unit 22, when the user enters a terminating instruction and the terminating instruction is not the instruction for terminating the treatment, it becomes possible for the user to apply an operation input using the operation input device 2. When the user operates the operation input device 2, the operation input device 2 outputs an operation signal to the control signal generator 31. The control signal generator 31 acquires the operation signal output from the operation input device 2 in step S310. The control signal generator 31 determines whether a treatment is to be performed using the surgical instruments 6 or not based on whether a terminating instruction is input or not. If no terminating instruction is input and the user has indicated its intention to terminate the treatment as indicated by "Yes" in step S311, then the control signal generator 31 (i) discards the acquired operation signal, (ii) controls the display unit 3 or the like to display an operation termination of the manipulator 5 in step S312, and (iii) shuts down the manipulator system 1A in step S313. After the manipulator system 1A has been shut down, it can be operated again by a predetermined operation such as entering a terminating instruction. If a terminating instruction is input and the treatment is not to be terminated as indicated by "No" in step S311, the control signal generator 31 generates a control signal depending on an operation signal, and outputs the control signal to the output unit 32 in step S314. The output unit 32 outputs a drive signal for actuating the drive unit 22 according to the control signal to the drive unit 22 via the cutoff unit 33 in step S316. When the drive signal is output to the drive unit 22 and the electric motor 23 of the drive unit 22 is energized, the drive unit encoder 24 and the driven unit encoder 27 that are mechanically coupled to the electric motor 23 are actuated by drive power generated by the electric motor 23. The drive unit encoder 24 and the driven unit encoder 27 now generate respective pulse signals. As with the first embodiment, a first operation quantity Ca is acquired for feedback control in step S316, and control goes back to step S310. After the driven unit 15 of each of the surgical instruments 6 is attached to the drive unit 22, the manipulator system 1A is in a state in which the drive unit 22 can actuate the surgical instrument 6 to perform a treatment. In this state, the manipulator control device 30A performs a monitoring process for a failure determination using the first determining unit 46 and the second determining unit 47, see step S200 in the first embodiment.

After the driven unit 15 of each of the surgical instruments 6 is attached to the drive unit 22, it is repeatedly determined whether the surgical instrument 6 is properly attached to the drive unit 22 or not in step S317. After the driven unit 15 of each of the surgical instruments 6 is attached to the drive unit 22, if the surgical instrument 6 is detached from the drive unit 22 or inappropriately attached to the drive unit 22, it is determined that the surgical instrument 6 is not appropriately attached to the drive unit 22 as indicated by "No" in step S317. Control goes back to step S306, for example and the manipulator system 1A enters the mode for waiting for the surgical instruments 6 to be attached in step S308. In the monitoring process for a failure determination using only the second determining unit 47 in step S400 depicted in FIG. 14, a first operation quantity Ca and a second operation quantity Cb are calculated in step S401, as depicted in FIG. 15. The second determining unit 47 determines whether the absolute value of the difference between the first operation quantity Ca and the second operation quantity Cb is larger than the third threshold value R3 or not in step S402. If the absolute value of the difference between the first operation quantity Ca and the second operation quantity Cb is larger than the third threshold value R3 as indicated by "Yes" in step S402, then the second determining unit 47 outputs a second cutoff signal to the cutoff unit 33 in step S403. An error message is displayed on the display unit 3 or the like in step S404, and the manipulator system 1A is shut down in step S313.

According to the present embodiment, as described hereinbefore, when the driven unit 15 is not attached to the drive unit 22, a failure of the drive unit encoder 24 and the driven unit encoder 27 is detected using the second determining unit 47, and when the driven unit 15 is attached to the drive unit 22, a failure of the drive unit encoder 24 is further detected using the first determining unit 46. The state in which the driven unit is attached to the drive unit 22 means the state in which a treatment is performed using the surgical instrument 6. In the event of a failure of each of the encoders, it is preferable to stop the surgical instrument 6 from operating more quickly than when the driven unit 15 is not attached to the drive unit 22. According to the present embodiment, when the driven unit 15 is attached to the drive unit 22, the connect/disconnect sensor 29 enables the mode selector 48 to permit the first determining unit 46 to operate. Consequently, in the state in which a treatment is performed using the surgical instrument 6, the manipulator system 1A can quickly enter a safe state, i.e., a state in which the surgical instruments 6 are shut off, in the event of a failure of the drive unit encoder 24.

Figure 18:
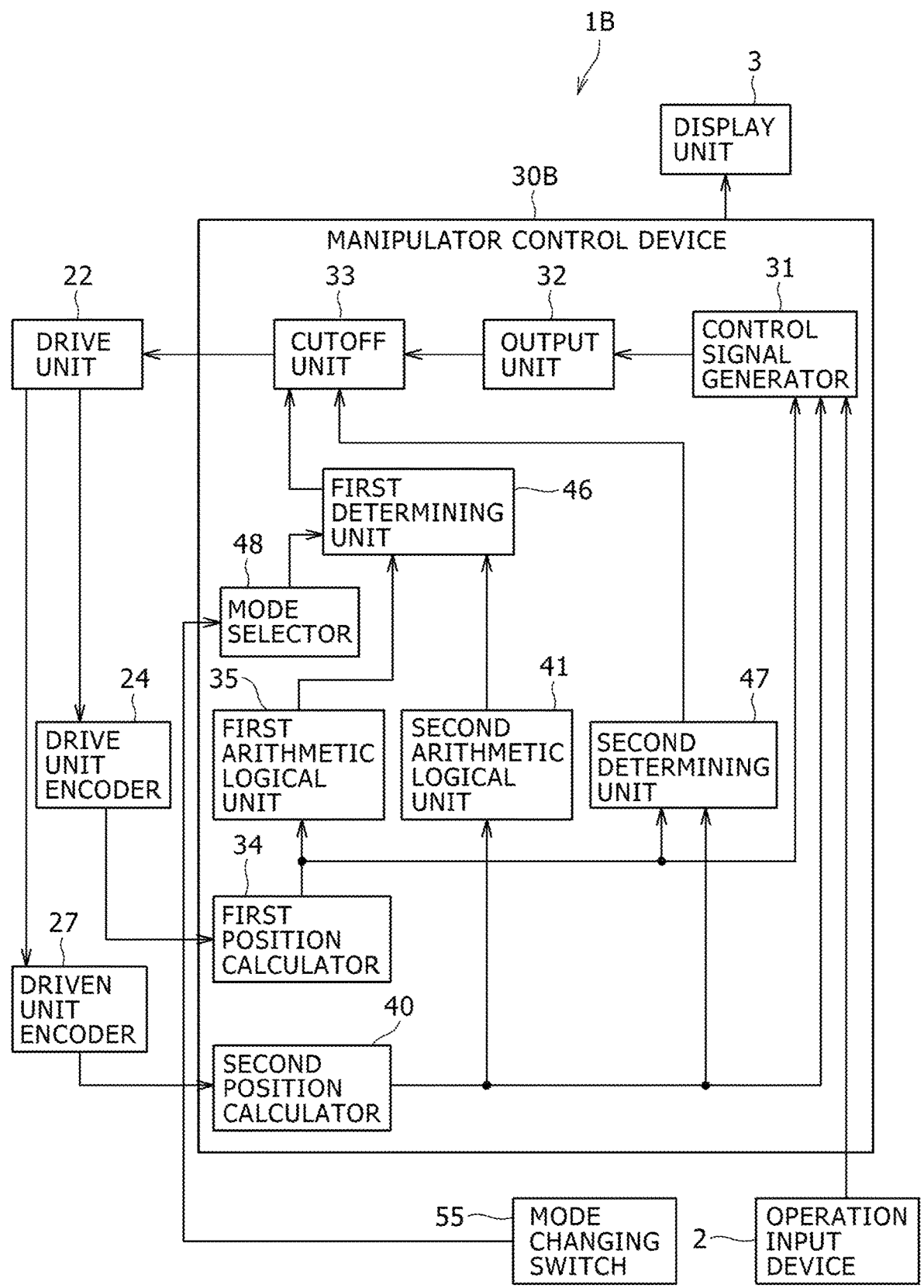
FIG. 18 is a block diagram of a manipulator system according to a third embodiment.

A third embodiment is now described hereinafter. FIG. 18 is a block diagram of a manipulator system 1B according to the third embodiment. The manipulator system 1B according to the present embodiment is different from the second embodiment described above in that rather than the connect/disconnect sensor 29 for detecting whether the drive unit 22 and the driven unit 15 are attached to one another or are detached from one another, a mode changing switch 55 is disposed on the operation input device 2. The mode changing switch 55 is electrically connected to a mode selector 48 of a manipulator control device 30B. The mode changing switch 55 may be of a known structure that can be operated by the user who uses the operation input device 2, such as a mechanical switch, a touch panel, or a GUI interface displayed on the display unit 3. The mode changing switch 55 is operated according to the instruction of the user who operates the manipulator system 1B to switch between (i) a mode in which both the first determining unit 46 and the second determining unit 47 are used and (ii) a mode in which the first determining unit 46 is not used and only the second determining unit 47 is used. Since the second determining unit 47 is always permitted to operate, the mode selector 48 is connected to the first determining unit 46 in order to selectively operate the first determining unit 46. The manipulator control device 30B may be arranged to display on the display unit 3 a message or the like for prompting the user to enter the mode in which both the first determining unit 46 and the second determining unit 47 are used, before a treatment using the surgical instruments 6 begins. Furthermore, the manipulator control device 30B may be arranged to inhibit itself from outputting the drive signal to the drive unit 22 until the manipulator system 1B enters the mode in which both the first determining unit 46 and the second determining unit 47 are used.

Figure 19:
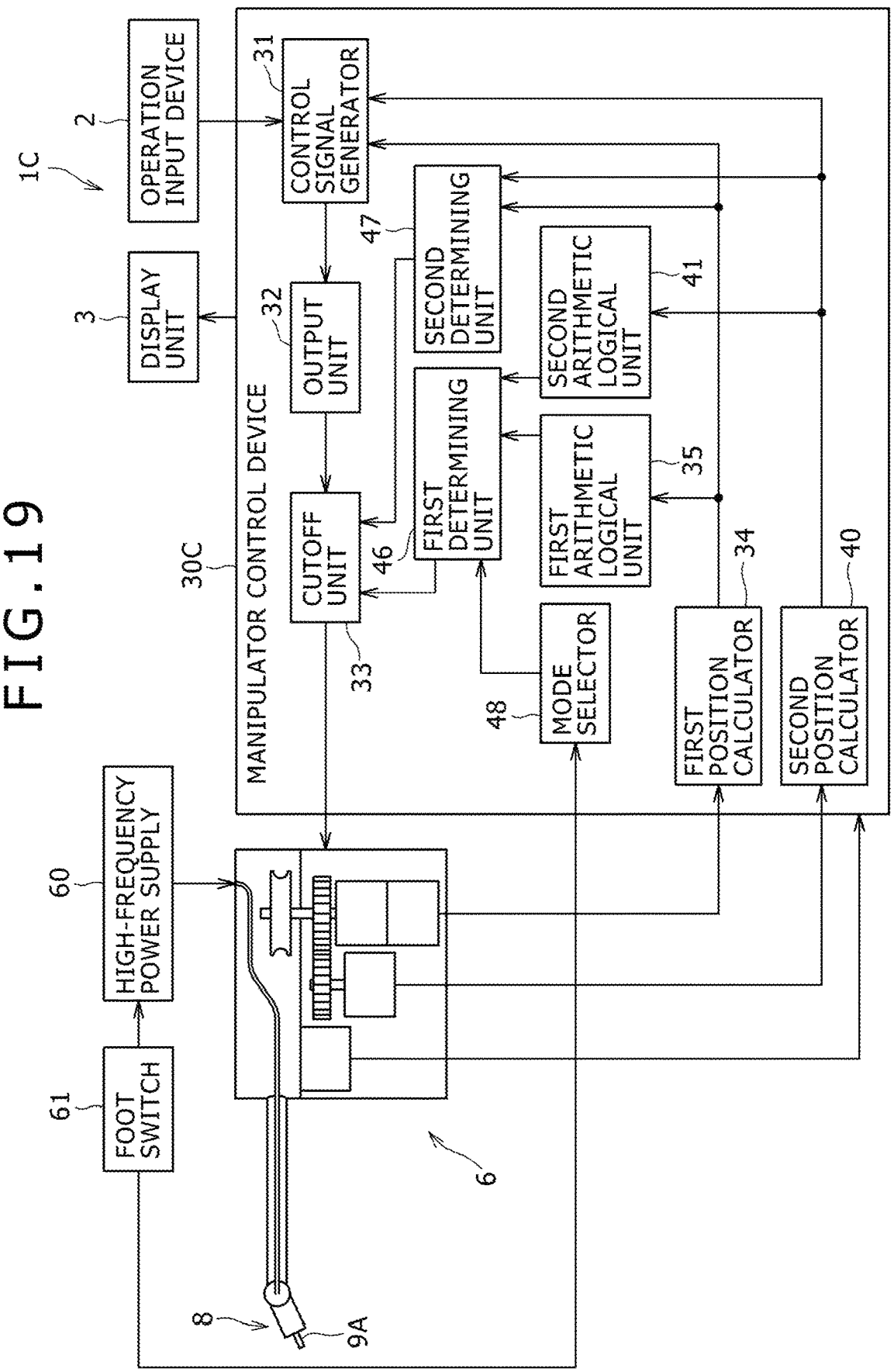
FIG. 19 is a block diagram of a manipulator system according to a fourth embodiment.

A fourth embodiment is now described hereinafter. FIG. 19 is a block diagram of a manipulator system 1C according to the fourth embodiment. The present embodiment is different from the previously described embodiments in that the manipulator system 1C performs a failure detection using both the first determining unit 46 and the second determining unit 47 when the manipulator system 1C operates using the treatment units 8 of the surgical instruments 6, and performs a failure detection using the second determining unit 47 while shutting off the first determining unit 46 when the manipulator system 1C does not use the treatment units 8. Each of the treatment units 8 of the surgical instruments 6 according to the present embodiment has a high-frequency knife 9A for incising a tissue with electric power supplied from a high-frequency power supply 60. The high-frequency knife 9A is not limited to any particular structure. The surgical instruments 6 according to the present embodiment may be of the monopolar type or the bipolar type.

The operation input device 2 includes a foot switch 61 for selectively turning on the high-frequency power supply 60 to supply electric power and turning off the high-frequency power supply 60 to stop supplying electric power. The foot switch 61 is electrically connected to the high-frequency power supply 60 and a manipulator control device 30C. The manipulator control device 30C has a mode selector 48 that is electrically connected to the foot switch 61. The mode selector 48 is connected to the foot switch 61 in order to be able to refer to whether an input is applied to the foot switch 61 or not. If there is no input applied to the foot switch 61, then the mode selector 48 inhibits the first determining unit 46 from operating and permits the second determining unit 47 to operate. If there is an input applied to the foot switch 61, then the mode selector 48 permits the first determining unit 46 and the second determining unit 47 to operate.

Figure 20:
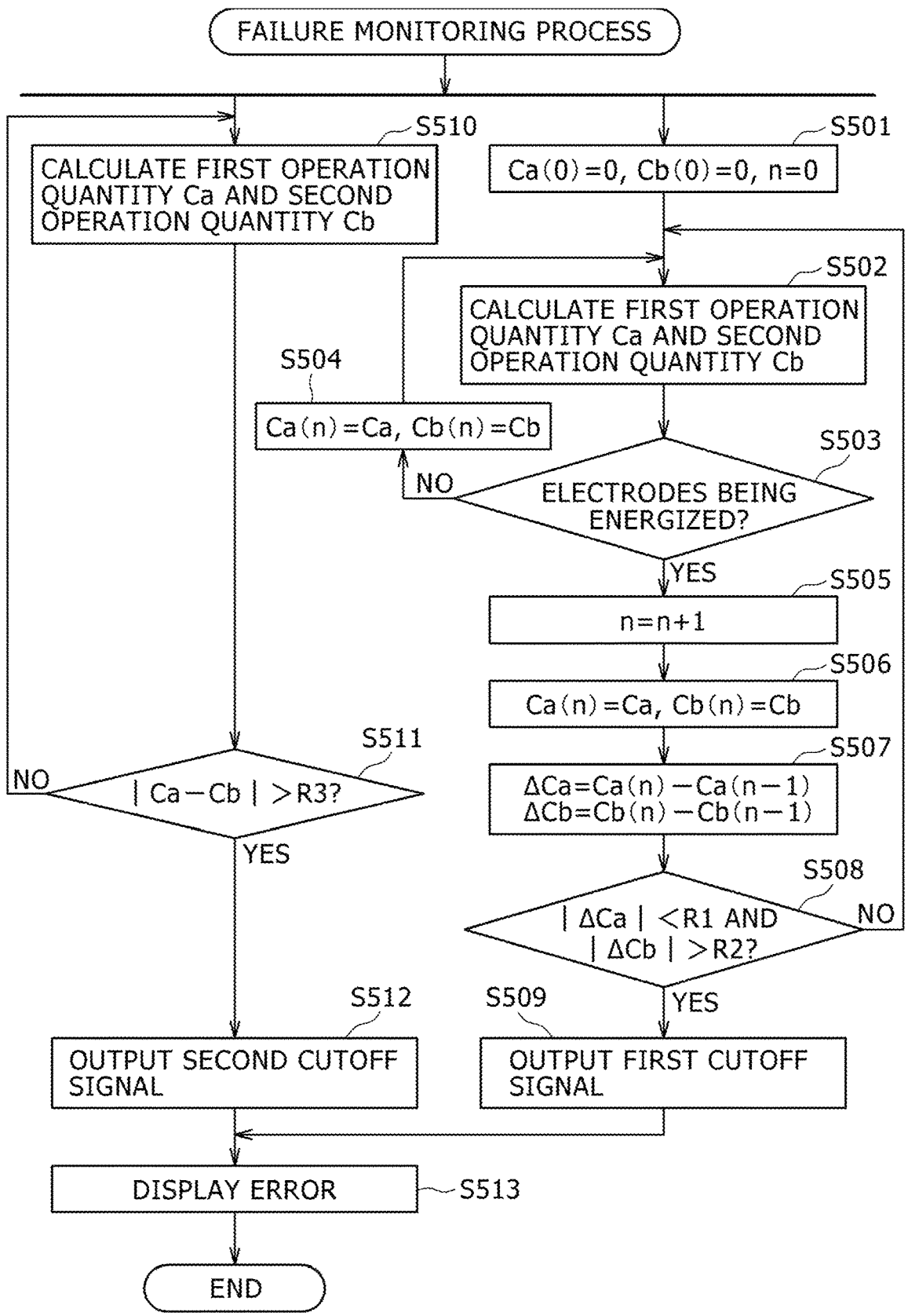
FIG. 20 is a flowchart depicting steps of operation of the manipulator system according to the fourth embodiment when in use.

Operation of the manipulator system 1C according to the present embodiment will be described below. FIG. 20 is a flowchart depicting a flow of operation of the manipulator system 1C according to the present embodiment when in use.

In the operation of the manipulator system 1C according to the present embodiment, a control process for the first determining unit 46 to output a first cutoff signal and a control process for the second determining unit 47 to output a second cutoff signal are carried out parallel to each other.

The control process for the first determining unit 46 to output a first cutoff signal is described hereinafter. As with the first embodiment, the first operation quantity $Ca(n)$, the second operation quantity $Cb(n)$, and the variable n are reset in step S501. Therefore, the initial value $Ca(0)$ of the first operation quantity Ca based on the pulse signal from the drive unit encoder 24 becomes 0, and the initial value $Cb(0)$ of the second operation quantity Cb based on the pulse signal from the driven unit encoder 27 becomes 0. Then, as with the first embodiment, based on the pulse signals output from the drive unit encoder 24 and the driven unit encoder 27 depending on the drive quantity of the drive unit 22, the first position calculator 34 calculates a first operation quantity Ca and the second position calculator 40 calculates a second operation quantity Cb in step S502. Then, the mode selector 48 branches the processing according to whether an input is applied to the foot switch 61 or not in step S503. If no input is applied to the foot switch 61 as indicated by "No" in step S503, then the mode selector 48 substitutes the latest first operation quantity Ca and second operation quantity Cb for the latest first operation quantity $Ca(n)$ and second operation quantity $Cb(n)$, respectively in step S504, after which control goes back to step S502. If an input is applied to the foot switch 61, then control goes to step S505 in which 1 is added to the variable n, after which control goes to step S506. In step S506, the first arithmetic logic unit 35 of the manipulator control device 30C substitutes the latest first operation quantity for the first operation quantity $Ca(n)$ corresponding to the variable n. The first arithmetic logic unit 35 stores the first operation quantity $Ca(n)$ in the position information memory 36. Furthermore, the second arithmetic logic unit 41 of the manipulator control device 30C substitutes the latest second operation quantity for the second operation quantity $Cb(n)$ corresponding to the variable n. The second arithmetic logic unit 41 stores the second operation quantity $Cb(n)$ in the position information memory 42.

Then, the manipulator control device 30C causes the difference arithmetic logic unit 37 of the first arithmetic logic unit 35 to calculate a first difference $\Delta Ca$ in step S507. The first difference $\Delta Ca$ represents a value calculated by subtracting a first operation quantity $Ca(n-1)$ from the latest first operation quantity $Ca(n)$. The first operation quantity $Ca(n-1)$ is acquired immediately before the latest first operation quantity $Ca(n)$. In step S507, furthermore, the manipulator control device 30C causes the difference arithmetic logic unit 43 of the second arithmetic logic unit 41 to calculate a second difference $\Delta Cb$. The second difference $\Delta Cb$ represents a value calculated by subtracting a second operation quantity $Cb(n-1)$ from the latest second operation quantity $Cb(n)$. The second operation quantity $Cb(n-1)$ is acquired immediately before the latest second operation quantity $Cb(n)$. The first difference $\Delta Ca$ and the second difference $\Delta Cb$ are output to the first determining unit 46. Then, the manipulator control device 30C causes the first determining unit 46 to branch the processing based on (i) the result of comparison between the absolute value of the first difference $\Delta Ca$ and the first threshold value R1 and (ii) the result of comparison between the absolute value of the second difference $\Delta Cb$ and the second threshold value R2 in step S508. If the absolute value of the first difference $\Delta Ca$ is smaller than the first threshold value R1 and the absolute value of the second difference $\Delta Cb$ is larger than the second threshold value R2, then the first determining unit 46 outputs a first cutoff signal for deactivating the drive unit 22 to the cutoff unit 33 in step S509. If the absolute value of the first difference $\Delta Ca$ is equal to or larger than the first threshold value R1 or the absolute value of the second difference $\Delta Cb$ is equal to or smaller than the second threshold value R2, then the first determining unit 46 does not output a first cutoff signal, and control goes back to step S502.

The control process for the second determining unit 47 to output a second cutoff signal is now described hereinafter. The second determining unit 47 calculates a latest first operation quantity Ca and a latest second operation quantity Cb by referring to the first position calculator 34 and the second position calculator 40 in step S510. Moreover, the second determining unit 47 compares the absolute value of the difference between the first operation quantity Ca and the second operation quantity Cb with the third threshold value R3 in step S511. If the absolute value of the difference between the first operation quantity Ca and the second operation quantity Cb is larger than the third threshold value R3 as indicated by "Yes" in step S511, then the second determining unit 47 outputs a second cutoff signal to the cutoff unit 33 in step S512. If the absolute value of the difference between the first operation quantity Ca and the second operation quantity Cb is equal to or smaller than the third threshold value R3 as indicated by "No" in step S511, then the second determining unit 47 does not output a second cutoff signal to the cutoff unit 33, and control goes back to step S510. As described, when at least either one of first and second cutoff signals is thus output to the cutoff unit 33, the drive unit 22 is not actuated, stopping the surgical instruments 6 from operating, even if an operation is input to the operation input device 2. After the surgical instruments 6 have been stopped from operating by at least either one of first and second cutoff signals output to the cutoff unit 33, the manipulator control device 30C outputs to the display unit 3 or the like a message indicating that the manipulator system 1C including the surgical instruments 6 has been shut down due to a failure in step S513. Assume the situation that the user operates the foot switch 61 to turn on or off the supply of electric power from the high-frequency power supply 60. When the user operates the foot switch 61 to turn on the supply of electric power, the mode selector 48 of the manipulator control device 30C of the present embodiment operates the manipulator control device 30C in a mode capable of performing a failure determination using the first determining unit 46 and the second determining unit 47. When the operator turns off the supply of electric power using the foot switch 61, the mode selector 48 operates the manipulator control device 30C in a mode capable of performing a failure determination not using the first determining unit 46 but using the second determining unit 47.

The manipulator control device 30C according to the present embodiment performs a failure determination using the first determining unit 46 and a failure determination using the second determining unit 47 parallel to each other. In the absence of an input to the foot switch 61 for turning on the supply of electric power from the high-frequency power supply 60, a failure determination using the first determining unit 46 is not performed. In the presence of an input to the foot switch 61 for turning on the supply of electric power from the high-frequency power supply 60, a failure determination using the first determining unit 46 is performed which is capable of detecting a failure of the drive unit encoder 24 more quickly than a failure determination using the second determining unit 47. While the supply of electric power using the high-frequency power supply 60 is turned on, the high-frequency knife 9A of the treatment unit 8 is energized with a high-frequency current. Therefore, in the event of a failure of the encoder while the energized high-frequency knife 9A is in use, it is preferable to quickly shut off the surgical instrument 6 including the high-frequency knife 9A. According to the present embodiment, since a failure determination using the first determining unit 46 can be performed while the supply of electric power supplied to the high-frequency knife 9A is turned on, the surgical instrument 6 can shut off particularly quickly in the event of a failure of the drive unit encoder 24 while the high-frequency knife 9A is energized.

Figure 21:
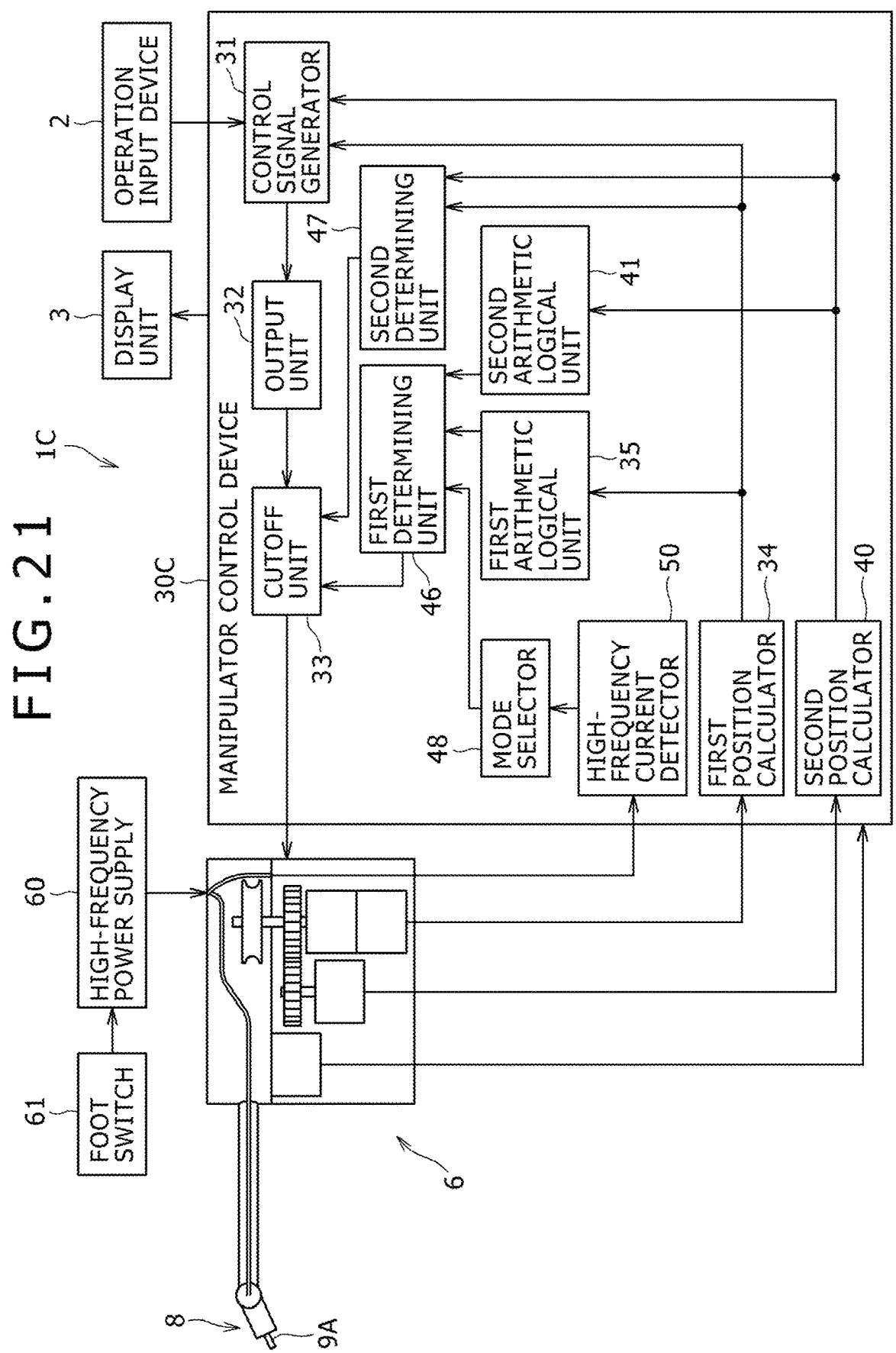
FIG. 21 is a block diagram depicting a configuration of a modification of the fourth embodiment.

A modification of the fourth embodiment is now described. FIG. 21 is a block diagram depicting a configuration of the modification of the present embodiment. According to the present modification, rather than the foot switch 61 connected to the manipulator control device 30C, a wire for sending a high-frequency current output from the high-frequency power supply 60 to the treatment unit 8 is connected to the manipulator control device 30C. The manipulator control device 30C has a high-frequency current detector 50 connected to a wire branched from the wire extending from the high-frequency power supply 60 to the treatment unit 8. The high-frequency current detector 50 controls the mode selector 48 depending on the supply of a high-frequency current. According to the present modification, if the supply of a high-frequency current is turned on, then the manipulator control device 30C operates in a mode in which a failure determination is performed using both the first determining unit 46 and the second determining unit 47. If the supply of a high-frequency current is turned off, then the manipulator control device 30C operates in a mode in which a failure determination is performed not using the first determining unit 46 and using the second determining unit 47. The high-frequency current detector 50 can directly detect when a high-frequency current is supplied to the treatment unit 8. Therefore, even if there is a time difference between an operation of the foot switch 61 and a switching of the supply of a high-frequency current, it is possible to perform a failure determination using both the first determining unit 46 and the second determining unit 47 while a high-frequency current is supplied.

In sum, one aspect of the disclosed technology is directed to a manipulator system comprises a power source configured to generate drive power for operating a surgical instrument. A first sensor is configured to detect a first detected value corresponding to a drive quantity of the power source. A second sensor is configured to detect a second detected value corresponding to a drive quantity of the power source. An arithmetic logic unit is configured to calculate an operation quantity of the power source per unit time as a first operation quantity based on the first detected value and calculate an operation quantity of the power source per unit time as a second operation quantity based on the second detected value. An operation input device operable by a user for entering an input. A control signal generator is configured to receive a signal output from the operation input device and generate a control signal for operating the surgical instrument. An output unit is configured to receive the control signal generated by the control signal generator and generate a drive signal for energizing the power source. A determining unit is configured to output a shutoff signal for de-energizing the power source if the first operation quantity is smaller than a first threshold value and the second operation quantity is larger than a second threshold value. The first threshold value is equal to or smaller than the second threshold value. A cutoff unit is configured to cut off the drive signal output from the output unit to the power source in response to the shutoff signal output for de-energizing the power source from the determining unit.

The determining unit is configured to output the shutoff signal if the absolute value of the difference between the first operation quantity calculated based on the first detected value and the second operation quantity calculated based on the second detected value is larger than a third threshold value. And when the first operation quantity is larger than the first threshold value or the second operation quantity is smaller than the second threshold value. The power source of the manipulator system is detachably attached to the surgical instrument and is capable of transmitting the drive power to the surgical instrument when the power source is attached to the surgical instrument. The power source has a connect/disconnect sensor configured to output a connect signal to the determining unit when the surgical instrument and the power source are attached to one another. The determining unit of the manipulator system is configured to output the shutoff signal when the connect signal is input to the determining unit and when the first operation quantity is smaller than the first threshold value and the second operation quantity is larger than the second threshold value.

The manipulator system further comprises an operation unit configured to operate the surgical instrument and the surgical instrument includes an electrode for treating a tissue. The operation unit includes a switch for selectively turning on and off the supply of an electric current to the electrode. The determining unit is configured to calculate a result of comparison between the absolute value of the difference between the first operation quantity calculated based on the first detected value and the second operation quantity calculated based on the second detected value with a third threshold value. In case the supply of an electric current to the electrode is turned off and is configured to output the shutoff signal based on the result of comparison. The determining unit outputs the shutoff signal if the first operation quantity is smaller than the first threshold value and the second operation quantity is larger than the second threshold value, in case the supply of an electric current to the electrode is turned on.

Another aspect of the disclosed technology is directed to a manipulator system comprises an elongated member having at least one joint. An operation input device operable by a user for entering an input. A drive unit is configured to output drive power for actuating the joint in response to the input from the operation input device. A transmitted member rotatable by the drive power output from the drive unit and transmitted thereto. A first sensor is configured to be attached to the drive unit and detects over time an angular displacement of the drive unit when the drive unit actuates the joint and output a first detected value representing the detected angular displacement. A second sensor is configured to be attached to the transmitted member and detects over time an angular displacement of the transmitted member when the drive unit actuates the joint and output a second detected value representing the detected angular displacement. At least one manipulator control device is configured to calculate a first difference representing a change over time in the angular displacement based on the first detected value and a second difference representing a change over time in the angular displacement based on the second detected value. At least one manipulator control device compares the first difference and a first threshold value with one another and compares the second difference and a second threshold value with one another and then controls the drive unit to de-energize the drive unit if the first difference is smaller than the first threshold value and the second difference is larger than the second threshold value.

Although the embodiments of the technology disclosed herein have been described in detail above with reference to the drawings, specific configurational details are not limited to those embodiments, but may include design changes or the like without departing from the scope of the invention. The components illustrated in the above embodiments and modifications may be arranged in appropriate combinations. The present invention is applicable to a manipulator system including remotely controlled surgical instruments.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A manipulator system comprising:
a power source configured to generate drive power for operating a surgical instrument;
a first sensor configured to detect a first detected value corresponding to a drive quantity of the power source;
a second sensor configured to detect a second detected value corresponding to a drive quantity of the power source; and
a computer comprising one or more processors configured to:
calculate an operation quantity of the power source per unit time as a first operation quantity based on the first detected value;
calculate an operation quantity of the power source per unit time as a second operation quantity based on the second detected value;
generate a control signal for operating the surgical instrument based on a signal output from an operation input device operable by a user for entering an input;
generate a drive signal for energizing the power source based on the control signal generated;
determine whether the first operation quantity is smaller than a first threshold value and the second operation quantity is larger than a second threshold value;
output a shutoff signal for de-energizing the power source in response to determining that the first operation quantity is smaller than the first threshold value and the second operation quantity is larger than the second threshold value; and
cut off output of the drive signal to the power source in response to the shutoff signal output for de-energizing the power source.

2. The manipulator system of claim 1,
wherein the computer is configured to:
determine whether the absolute value of the difference between the first operation quantity calculated based on the first detected value and the second operation quantity calculated based on the second detected value is larger than a third threshold value in response to determining that the first operation quantity is now smaller than the first threshold value or the second operation quantity is not larger than the second threshold value; and
output the shutoff signal in response to determining that the absolute value of the difference between the first operation quantity and the second operation quantity is larger than the third threshold value.

3. The manipulator system of claim 1,
wherein the power source is configured to:
be detachably attached to the surgical instrument; and
transmit the drive power to the surgical instrument when the power source is attached to the surgical instrument.

4. The manipulator system of claim 1,
wherein the power source comprises:
a connect/disconnect sensor configured to:
detect that the surgical instrument and the power source are attached to one another; and
output a connect signal to the computer in response to detecting that the surgical instrument and the power source are attached to one another.

5. The manipulator system of claim 4,
wherein the computer is configured to:
output the shutoff signal in response to:
receiving the connect signal output from the connect/disconnect sensor of the power source; and
determining that the first operation quantity is smaller than the first threshold value and the second operation quantity is larger than the second threshold value.

6. The manipulator system of claim 1,
wherein the first threshold value is equal to or smaller than the second threshold value.

7. The manipulator system of claim 1,
wherein the surgical instrument comprises an electrode for treating a tissue,
wherein the computer is configured to:
selective turn on and off supply of an electric current to the electrode in accordance with an input from a switch;
calculate a result of comparison between the absolute value of the difference between the first operation quantity calculated based on the first detected value and the second operation quantity calculated based on the second detected value with a third threshold value in response to the supply of the electric current to the electrode being turned off;
output the shutoff signal based on the result of comparison; and
output the shutoff signal in response to determining that the first operation quantity is smaller than the first threshold value and the second operation quantity is larger than the second threshold value, and the supply of the electric current to the electrode being turned on.

8. A manipulator system comprising:
an elongated member comprising at least one joint;
an operation input device operable by a user for entering an input;
a drive unit configured to output drive power for actuating the at least one joint in response to the input from the operation input device;
a transmitted member configured to be rotated by the drive power output from the drive unit and transmitted thereto;
a first sensor attached to the drive unit, and configured to detect over time an angular displacement of the drive unit when the drive unit actuates the at least one joint and to output a first detected value representing the angular displacement detected;
a second sensor attached to the transmitted member, and configured to detect over time an angular displacement of the transmitted member when the drive unit actuates the at least one joint and to output a second detected value representing the angular displacement detected; and
a computer comprising one or more processors configured to:
calculate a first difference representing a change over time in the angular displacement based on the first detected value;
calculate a second difference representing a change over time in the angular displacement based on the second detected value;
determine whether the first difference is smaller than a first threshold value and the second difference is larger than a second threshold value; and control the drive unit to de-energize the drive unit in
response to determining that the first difference is
smaller than the first threshold value and the second
difference is larger than the second threshold value.

* * * * *